(12) United States Patent
Logan

(10) Patent No.: US 10,313,714 B2
(45) Date of Patent: Jun. 4, 2019

(54) AUDIOVISUAL CONTENT PRESENTATION DEPENDENT ON METADATA

(71) Applicant: TiVo Solutions Inc., San Carlos, CA (US)

(72) Inventor: James D. Logan, Windham, NH (US)

(73) Assignee: TIVO SOLUTIONS INC., San Jose, CA (US)

(\*) Notice: Subject to any disclaimer, the term of this patent is extended or adjusted under 35 U.S.C. 154(b) by 13 days.

(21) Appl. No.: 14/284,367

(22) Filed: May 21, 2014

(65) Prior Publication Data
US 2015/0082338 A1 Mar. 19, 2015

Related U.S. Application Data

(63) Continuation of application No. 10/060,001, filed on Jan. 29, 2002, and a continuation-in-part of
(Continued)

(51) Int. Cl.
*H04N 7/10* (2006.01)
*H04N 7/025* (2006.01)
(Continued)

(52) U.S. Cl.
CPC .......... *H04N 21/23424* (2013.01); *A23L 2/52* (2013.01); *A23L 33/105* (2016.08); *A61K 8/553* (2013.01); *A61K 8/60* (2013.01); *A61K 8/68* (2013.01); *A61K 8/97* (2013.01); *A61K 9/0014* (2013.01); *A61K 36/48* (2013.01); *A61K 36/54* (2013.01); *A61K 47/24* (2013.01);
*A61Q 5/02* (2013.01); *A61Q 19/00* (2013.01); *H04H 20/28* (2013.01); *H04H 20/93* (2013.01);
(Continued)

(58) Field of Classification Search
CPC ......... H04N 21/25891; H04N 21/4331; H04N 21/44008; H04N 21/4661; H04N 21/4825; H04N 21/6156; H04N 21/84
See application file for complete search history.

(56) References Cited

U.S. PATENT DOCUMENTS 5,892,536 A * 4/1999 Logan .................. H04H 20/106
348/E7.075
5,911,029 A * 6/1999 Sakaguchi ........... G11B 15/026
358/908

(Continued)

OTHER PUBLICATIONS

United States Patent and Trademark Office, U.S. Appl. No. 13/271,892, Non-Final Office Action dated Mar. 26, 2014, Mar. 26, 2014.
(Continued)

*Primary Examiner* — Joshua D Taylor
(74) *Attorney, Agent, or Firm* — Haley Guiliano LLP

(57) ABSTRACT

A system for utilizing metadata created either at a central location for shared use by connected users, or at each individual user's location, to enhance user's enjoyment of available broadcast programming content. A variety of mechanisms are employed for automatically and manually identifying and designating programming segments, associating descriptive metadata which the identified segments, distributing the metadata for use at client locations, and using the supplied metadata to selectively record and playback desired programming.

6 Claims, 1 Drawing Sheet

Related U.S. Application Data application No. 09/536,969, filed on Mar. 28, 2000, now Pat. No. 6,931,451.

(60) Provisional application No. 60/336,602, filed on Dec. 3, 2001, provisional application No. 60/304,570, filed on Jul. 11, 2001, provisional application No. 60/264,868, filed on Jan. 29, 2001.

(51) Int. Cl.

| | | |
|---|---|---|
| *H04N 21/234* | (2011.01) | |
| *A23L 2/52* | (2006.01) | |
| *A61K 8/55* | (2006.01) | |
| *A61K 8/60* | (2006.01) | |
| *A61K 8/68* | (2006.01) | |
| *A61K 8/97* | (2017.01) | |
| *A61K 9/00* | (2006.01) | |
| *A61K 36/48* | (2006.01) | |
| *A61K 36/54* | (2006.01) | |
| *A61K 47/24* | (2006.01) | |
| *A61Q 5/02* | (2006.01) | |
| *A61Q 19/00* | (2006.01) | |
| *H04H 20/28* | (2008.01) | |
| *H04H 20/93* | (2008.01) | |
| *H04H 60/27* | (2008.01) | |
| *H04H 60/46* | (2008.01) | |
| *H04H 60/73* | (2008.01) | |
| *H04H 60/74* | (2008.01) | |
| *H04H 60/80* | (2008.01) | |
| *H04N 5/44* | (2011.01) | |
| *H04N 5/76* | (2006.01) | |
| *H04N 7/173* | (2011.01) | |
| *H04N 21/258* | (2011.01) | |
| *H04N 21/4147* | (2011.01) | |
| *H04N 21/433* | (2011.01) | |
| *H04N 21/4335* | (2011.01) | |
| *H04N 21/439* | (2011.01) | |
| *H04N 21/44* | (2011.01) | |
| *H04N 21/442* | (2011.01) | |
| *H04N 21/45* | (2011.01) | |
| *H04N 21/458* | (2011.01) | |
| *H04N 21/462* | (2011.01) | |
| *H04N 21/466* | (2011.01) | |
| *H04N 21/472* | (2011.01) | |
| *H04N 21/475* | (2011.01) | |
| *H04N 21/4788* | (2011.01) | |
| *H04N 21/482* | (2011.01) | |
| *H04N 21/6543* | (2011.01) | |
| *H04N 21/81* | (2011.01) | |
| *H04N 21/8352* | (2011.01) | |
| *H04N 21/84* | (2011.01) | |
| *H04N 21/845* | (2011.01) | |
| *H04N 21/8547* | (2011.01) | |
| *H04N 21/858* | (2011.01) | |
| *H04N 21/61* | (2011.01) | |
| *A23L 33/105* | (2016.01) | |
| *A61K 36/899* | (2006.01) | |
| *H04H 60/37* | (2008.01) | |
| *H04N 7/088* | (2006.01) | |
| *H04N 9/82* | (2006.01) | |

(52) U.S. Cl.
CPC ............ *H04H 60/27* (2013.01); *H04H 60/46* (2013.01); *H04H 60/73* (2013.01); *H04H 60/74* (2013.01); *H04H 60/80* (2013.01); *H04N 5/4401* (2013.01); *H04N 5/76* (2013.01); *H04N 7/17318* (2013.01); *H04N 21/25891* (2013.01); *H04N 21/4147* (2013.01); *H04N 21/439* (2013.01); *H04N 21/4331* (2013.01); *H04N 21/4334* (2013.01); *H04N 21/4335* (2013.01); *H04N 21/44008* (2013.01); *H04N 21/44213* (2013.01); *H04N 21/44222* (2013.01); *H04N 21/458* (2013.01); *H04N 21/4532* (2013.01); *H04N 21/4622* (2013.01); *H04N 21/4661* (2013.01); *H04N 21/4663* (2013.01); *H04N 21/4668* (2013.01); *H04N 21/4756* (2013.01); *H04N 21/4788* (2013.01); *H04N 21/47205* (2013.01); *H04N 21/47214* (2013.01); *H04N 21/4825* (2013.01); *H04N 21/4826* (2013.01); *H04N 21/6156* (2013.01); *H04N 21/6543* (2013.01); *H04N 21/812* (2013.01); *H04N 21/8352* (2013.01); *H04N 21/84* (2013.01); *H04N 21/8456* (2013.01); *H04N 21/8547* (2013.01); *H04N 21/8586* (2013.01); *A61K 36/899* (2013.01); *A61K 2800/782* (2013.01); *H04H 60/37* (2013.01); *H04N 7/088* (2013.01); *H04N 9/8205* (2013.01); *H04N 21/482* (2013.01)

(56) References Cited

U.S. PATENT DOCUMENTS

| | | | | |
|---|---|---|---|---|
| 5,966,120 | A * | 10/1999 | Arazi | H04N 21/23424 345/12 |
| 5,999,689 | A * | 12/1999 | Iggulden | G11B 27/28 348/460 |
| 6,002,394 | A | 12/1999 | Schein et al. | |
| 6,144,375 | A | 11/2000 | Jain et al. | |
| 6,289,165 | B1 | 9/2001 | Abecassis | |
| 6,330,334 | B1 * | 12/2001 | Ryan | G11B 20/00086 348/E5.123 |
| 6,442,326 | B1 * | 8/2002 | Kaneko | H04H 60/06 358/908 |
| 6,470,356 | B1 * | 10/2002 | Suzuki | G06F 17/30017 |
| 6,546,556 | B1 * | 4/2003 | Kataoka | H04N 7/088 348/465 |
| 6,600,874 | B1 * | 7/2003 | Fujita | G11B 20/10 386/249 |
| 6,637,032 | B1 * | 10/2003 | Feinleib | G06F 17/30017 348/552 |
| 6,850,252 | B1 * | 2/2005 | Hoffberg | G06K 9/00369 348/E7.061 |
| 6,993,245 | B1 * | 1/2006 | Harville | H04N 5/76 348/E7.061 |
| 7,080,392 | B1 * | 7/2006 | Geshwind | H04N 5/76 348/E7.031 |
| 7,269,330 | B1 * | 9/2007 | Iggulden | H04H 60/375 348/460 |
| 7,319,806 | B1 | 1/2008 | Willner et al. | |
| 7,624,337 | B2 | 11/2009 | Sull et al. | |
| 7,631,327 | B2 | 12/2009 | Dempski et al. | |
| 7,877,774 | B1 * | 1/2011 | Basso | G06F 17/3002 725/115 |
| 9,639,254 | B2 * | 5/2017 | Lussier | G11B 27/034 |
| 9,684,728 | B2 * | 6/2017 | Lynn | G06F 17/30876 |
| 2001/0036865 | A1 | 11/2001 | Neal | |
| 2001/0047298 | A1 | 11/2001 | Moore et al. | |
| 2002/0054083 | A1 * | 5/2002 | Boreczky | G06F 3/0481 715/738 |
| 2002/0083473 | A1 * | 6/2002 | Agnihotri | G11B 27/105 725/140 |
| 2002/0166123 | A1 | 11/2002 | Schrader et al. | |
| 2003/0079224 | A1 | 4/2003 | Komar et al. | |
| 2003/0088612 | A1 * | 5/2003 | Goldschmidt Iki | H04N 5/44543 709/202 |
| 2004/0201784 | A9 * | 10/2004 | Dagtas | G06F 17/30787 348/738 |

(56) References Cited

U.S. PATENT DOCUMENTS

| | | | |
|---|---|---|---|
| 2005/0060741 A1 | 3/2005 | Tsutsui et al. | |
| 2005/0086703 A1* | 4/2005 | Gupta | G06F 17/241 725/135 |
| 2005/0144641 A1 | 6/2005 | Lewis | |
| 2005/0262539 A1* | 11/2005 | Barton | G11B 27/034 725/90 |
| 2009/0265737 A1* | 10/2009 | Issa | G06F 17/30817 725/38 |
| 2010/0242072 A1* | 9/2010 | Bhagavath | H04N 21/235 725/94 |
| 2012/0159539 A1* | 6/2012 | Berberet | H04N 7/17336 725/34 |
| 2013/0017890 A1 | 1/2013 | Leen et al. | |
| 2015/0237383 A1* | 8/2015 | Riedl | H04N 21/2385 725/35 |
| 2015/0365725 A1* | 12/2015 | Belyaev | H04N 21/458 725/46 |
| 2016/0029059 A1 | 1/2016 | Logan et al. | |
| 2016/0255407 A1* | 9/2016 | Hassell | H04N 5/44543 386/297 |

OTHER PUBLICATIONS

United States Patent and Trademark Office, U.S. Appl. No. 13/271,892, Final Office Action dated Jan. 22, 2015, Jan. 22, 2015.
United States Patent and Trademark Office, U.S. Appl. No. 13/271,892, Non-Final Office Action dated Aug. 13, 2015, Aug. 13, 2015.
United States Patent and Trademark Office, U.S. Appl. No. 13/271,892, Final Office Action dated Jan. 29, 2016, Jan. 29, 2016.
United States Patent and Trademark Office, U.S. Appl. No. 14/639,016, Non-Final Office Action dated Jul. 20, 2016, Jul. 20, 2016.

* cited by examiner

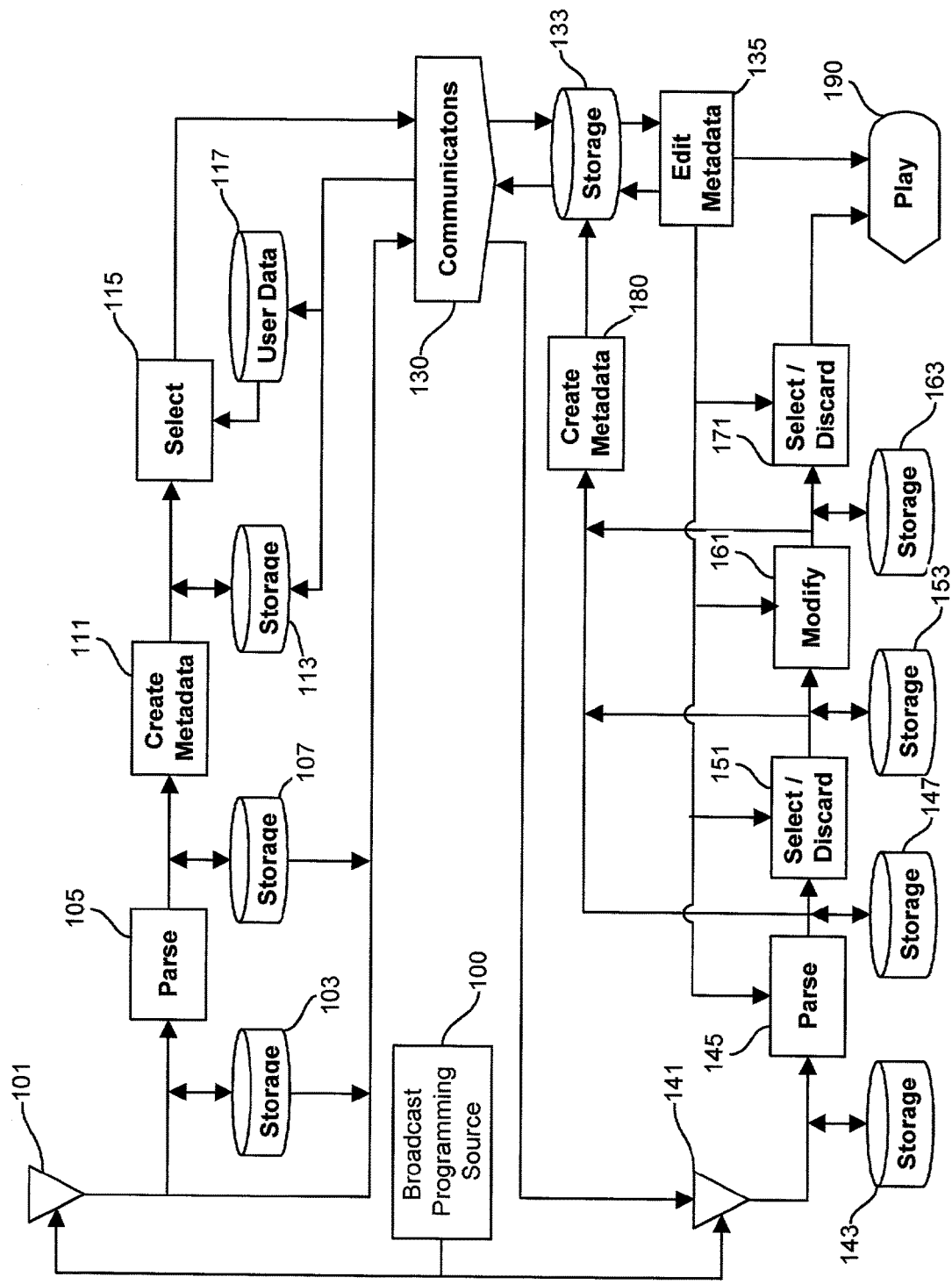

AUDIOVISUAL CONTENT PRESENTATION DEPENDENT ON METADATA

CROSS REFERENCE TO RELATED APPLICATIONS

This application claims the benefit of the filing date of the following applications: U.S. Utility patent application Ser. No. 10/060,001, filed on Jan. 29, 2002 entitled "Audio and Video Program Recording, Editing and Playback Systems Using Metadata;" U.S. Utility patent application Ser. No. 09/536,969 filed on Mar. 28, 2000 entitled "Systems and Methods for Modifying Broadcast Programming;" U.S. Provisional Patent Application Ser. No. 60/264,868 filed on Jan. 29, 2001 entitled "Broadcast Television and Radio Recording, Editing and Playback Systems Using Metadata;" U.S. Provisional Application Ser. No. 60/304,570 filed on Jul. 11, 2001 entitled "Audio and Video Program Recording, Editing and Playback Systems using Metadata;" and U.S. Provisional Application Ser. No. 60/336,602 filed on Dec. 3, 2001 entitled "Methods and Apparatus for Automatically Bookmarking Programming Content." U.S. Utility patent application Ser. No. 10/060,001 is hereby incorporated by reference.

FIELD OF THE INVENTION

This invention relates to audio and video program reception, storage, editing, recording and playback systems and more particularly to methods and apparatus for distributing, recording, organizing and editing metadata that is used to selectively distribute, record, organize, edit and play program content.

BACKGROUND OF THE INVENTION

The present invention belong to a family of related systems that use metadata to control the playback of broadcast programming as disclosed in the previously issued patents and previously filed applications summarized below.

U.S. Pat. Nos. 5,892,536 and 5,986,692, issued to James D. Logan et al. describe systems which employ metadata to selectively store, manipulate and playback broadcast programming. Some of the novel arrangements and features disclosed in those two patents may be summarized as follows:

1. A remote editing station, which may be at the broadcast facility or at a remote location, classifies, describes or otherwise identifies individual segments of broadcast programming and sends metadata (sometimes referred to as "markup data") identifying and describing those segments to a remote client receiver. For example, the markup data may identify individual segments by specifying the source and the time of the original broadcast, or by specifying some other unique characteristic of the broadcast signal. The program segments may be TV, radio, or Internet programs, or portions of programs, including individual songs, advertisements, or scenes.

2. The communication link used to transmit the metadata to the client may take one of several forms, including the Internet, a dialup telephone link, the communications pathway used to carry the broadcast signals to the client, or other forms of communication used to transport the metadata to the client.

3. At the client receiver, the metadata is used to identify particular program segments that may then be manipulated in one or more of a variety of ways. For example, the metadata may be used to selectively play back or record particular segments desired by the user; to re-sequence the identified segments into a different time order; to "edit-out" undesired portions of identified segments; to splice new information, such as computer text or advertising, into identified segments for rendering with the program materials, or to substitute different material (e.g. dubbing in acceptable audio to replace profanity to make programming more acceptable to minors).

4. The client receives and locally stores incoming broadcast programming and uses the markup data to identify desired segments within the stored program materials. The local storage mechanism may advantageously include means for concurrently recording live broadcasting while replaying a delayed version of the previously recorded programming as described in U.S. Reissue Pat. 36,801 issued to James D. Logan et al.

5. The markup data can provide a detailed "electronic program guide" to the broadcast programming previously received and stored in a personal video recorder (PVR) or an audio storage device, permitting the user to selectively play back a desired segment or portion of the programming previously recorded.

6. The markup data may be used to create a recorded collection of desired segments extracted from the buffered broadcast, allowing the desired segments to be saved while the remainder of the buffered materials is discarded to conserve recording space.

7. Special markup signals may be selectively sent to individual subscribers based on his or her indicated preferences so that only preferred program segments are identified and processed. For example, a subscriber might request markup data only for sports and news.

U.S. Pat. No. 6,088,455 issued to James D. Logan et al. describes related systems that use a signal analyzer to extract identification signals from broadcast program segments. These identification signals are then sent as metadata to the client where they are compared with the received broadcast signal to identify desired program segments. For example, a user may specify that she likes Frank Sinatra, in which case she is provided with identification signals extracted from Sinatra's recordings which may be compared with the incoming broadcast programming content to identify the desired Sinatra music, which is then saved for playback when desired.

U.S. Utility patent application Ser. No. 09/536,969 filed by James D. Logan et al. on Mar. 28, 2000 describes further systems that employ metadata for selectively recording and/or reproducing received broadcast programming. The implementations disclosed in that application employ:

1. A receiver connected to record incoming broadcast signals and a PC connected to a web server via the Internet. A browser program running on the PC uses the web interface provided by the web server, selects songs of interest, downloads identification signals (e.g., extracted feature-sets or signatures) which uniquely identify the content of desired program segments (songs), which are then selectively saved for reproduction.

2. A signal processor that identifies characteristics of the stored programming (scene changes, voice vs. music, voices of particular people, etc.) that can be used to selectively store desired programming.

3. Identification signals derived from received broadcast programming at the client produce identification signals which are sent to a remote server which compares the received identification signals with a database at the server and returns attribute information to the client to describe recognized information. The attribute information can include the title of the segment, the name of the performing artist, albums that have a recording of this segment, etc.

4. Program segment files (e.g. songs) in a server library that are made available to those client locations which demonstrate that they are entitled to access the library copy by sending an identification signal to the server that is extracted from a copy of the desired segment already in the client's possession. Thereafter, a qualified client can obtain the authorized copy from the server from remote locations. Locally recorded programming can be uploaded from a client into the library, and such uploading can be "virtual" (that is, need not actually take place) when an equivalent copy of the same program segment is already stored in the server library.

U.S. Pat. Nos. 5,271,811, 5,732,216, and 6,199,076, and co-pending application Ser. No. 09/782,546 filed on Feb. 13, 2001, by James D. Logan et al. describe an audio program and message distribution system which incorporates the following features:

1. A host system organizes and transmits program segments to client subscriber locations.

2. A scheduling file of metadata schedules the content and sequence of a playback session, which may then be modified by the user.

3. The content of the scheduled programming is varied in accordance with preferences associated with each subscriber.

4. Program segments are associated with descriptive subject matter segments, and the subject matter segments may be used to generate both text and audio cataloging presentations to enable the user to more easily identify and select desirable programming.

5. A playback unit at the subscriber location reproduces the program segments received from the host and includes mechanisms for interactively navigating among the program segments.

6. A usage log is compiled to record the subscriber's use of the available program materials, to return data to the host for billing, to adaptively modify the subscriber's preferences based on actual usage, and to send subscriber-generated comments and requests to the host for processing.

7. Voice input and control mechanisms included in the player allow the user to perform hands-free navigation of the program materials and to dictate comments and messages, which are returned to the host for retransmission to other subscribers.

8. The program segments sent to each subscriber may include advertising materials, which the user can selectively play to obtain credits against the subscriber fee.

9. Parallel audio and text transcript files for at least selected programming enable subject matter searching and synchronization of the audio and text files.

10. Speech synthesis may be used to convert transcript files into audio format.

11. Image files may also be transmitted from the server for synchronized playback with the audio programming 12. A text transcript including embedded markup flags may be used to provide a programmed multimedia presentation including spoken audio text created by speech synthesis synchronized with presentation of images identified by the markup tags.

U.S. patent application Ser. No. 09/699,176 filed on Oct. 28, 2000 describes methods and apparatus for an advertising-supported system for delivering programming to a consumer in a protected form. The delivered programming can only be reproduced in its original form by a specific decryption process and is accompanied by at least one advertisement. The consumer uses a player device capable of performing the decryption process and reproducing the music in its original form only if the advertisement has been or is being presented to the consumer.

The disclosure of each of the foregoing patents and applications is incorporated herein by reference.

SUMMARY OF THE INVENTION

The present invention expands the capabilities of the systems described in the above-noted patents and applications by providing means at the user's location for creating metadata which may be used in combination with metadata provided by an external source, for editing metadata in various ways at the user's location, for automatically responding to user activity to generate new metadata which characterizes the user's preferences and which serves to automatically identify and describe (or rate) programming segments, and for responding in novel ways to the available metadata to enhance the utility and enjoyment of available broadcast materials.

In accordance with a feature of the invention, methods and apparatus are employed for selectively controlling the presentation of broadcast programming in which a user viewing or listening to broadcast programming at a first location may take advantage of the insights provided by a different viewer at another location in order to control the manner in which segments of the broadcast programming are recorded and/or replayed.

In accordance with this aspect of the invention, the broadcast programming is received at a first location and presented to a first user. Metadata is accepted from the first user that includes a designation of one or more specific segments of the broadcast programming together with a characterization of each segment which may take the form of a rating expressing the first user's opinion of the merit of the segment, a summary of the segment, a comment concerning the segment, or the like.

The metadata accepted from the first user is then transmitted to the second user at a second location. Programming received at the second location is then selectively stored and/or played back in a manner facilitated by the metadata supplied by the first user.

The specific features and advantages of the present invention may be more clearly understood by considering the following detailed description of a preferred embodiment of the invention. In the course of this description, frequent reference will be made to the attached drawing.

BRIEF DESCRIPTION OF THE DRAWING

FIG. 1 is a schematic block diagram that illustrates the functional components which are used in a preferred embodiment of invention and which operate at both a remote location and at one of the user locations to implement the invention.

DETAILED DESCRIPTION

The methods and apparatus contemplated by the present invention facilitate the selective storage, organization and reproduction (playback) of broadcast programming through the use of metadata that identifies and describes segments of that broadcast programming. This metadata can be created locally or at a remote site and transmitted to the user's location to enable the user to more effectively manage broadcast programming received at the user's location.

FIG. 1 illustrates in schematic form the manner in which information is processed in accordance with the invention. As will be described in more detail below, many of the structures and functions illustrated in FIG. 1 represent alternative or optional functionality that need not be present in all implementations of the invention.

At the remote location, broadcast programming from a source 100 is received at 101 and may be processed immediately or saved in a storage unit 103 for later processing. The incoming broadcast programming signals may be received as a live public broadcast, or may take the form of programming content received prior to the time of its later public broadcast. At 105, the incoming broadcast signals are parsed or subdivided into logically separate segments, which need not be contiguous and which may be overlapping or nested. The individual segments may be processed immediately after they are identified during the parsing process, or they may be stored for future processing in a storage unit 107.

As illustrated at 111, metadata is then created which describes each of the identified programming segments. The metadata describing each segment may take the form of a separate data entity, or may be stored or transmitted with the content of programming segment, which it describes. Unless the metadata is associated with a particular segment by being stored or transmitted with that segment, it includes a pointer or some other mechanism for specifying the segment or segments it describes. In addition, the metadata typically includes additional descriptive information about the associated segment(s). The metadata created at 111 may be immediately processed or transmitted to the user after it is created, or may be stored for later processing or transmission in a storage unit illustrated at 113.

Only selected items of metadata may be transmitted to the user location. The specific metadata transmitted may be selected as shown at 115 in a variety of ways. Data describing the demographics of individual users and data specifying user preferences stored at 117 may be used to selectively provide the user with only that portion of the available metadata which is best suited to the needs of the user or which a third party, such as an advertiser, desires to make available to the user.

Note that metadata created by the user, or preference data supplied by the user or derived from an analysis of the user's use of the system, or from the viewer's demographic characteristics, may be combined with or used instead of metadata and preference data created at the remote location.

Note also that the content of broadcast programming received at the remote site may be forwarded to the user location with or separately from the corresponding metadata. This content information may take the form of the broadcast programming received at the remote site at 101, previously received programming stored at 103, and individual segments as parsed at 106 and stored at 107. As noted above, the metadata associated with these programming signals may be combined with the programming content as transmitted to the user, or may be sent separately over the same or a different communications pathway.

The communication methods or apparatus used to transport metadata and/or content to the user as illustrated at 130 may take many different forms, including: the Internet, a dialup telephone connection through the public switched telephone network (PSTN), a wireless transmission system, cable, private line facilities, or data storage media transported from the content publisher and/or the metadata creator to the user. The communications may take place over a combination of such facilities and, as noted earlier, the content and metadata may be transmitted in one or both directions together or separately over the same or different facilities.

Metadata created at the remote location and transmitted via the communications facility 130 may be stored at 133 at the user location. The metadata stored at 133 may be edited at the user location as indicated at 135, and metadata from the user location may be returned via the communications facility 130 to the remote location for shared use by others.

At the user location, broadcast programming signals are received at 141, either in the form of a live public broadcast from the source 100, or as programming content received from the remote location via the communications link 130. It a leading purpose of the present invention to provide the user with a better and more convenient way to identify and reproduce that portion of the large quantity of programming that is broadcast for general consumption from many sources via many pathways, including conventional radio and television broadcasting, whether over the airwaves or via a cable or satellite facility. The metadata that is provided from the remote location via the communications pathway(s) 130 may be used to selectively store, organize and/or selectively reproduce programming received directly at the user location from a source 100, or received together or separately with the metadata via the pathway 130.

The broadcast programming content received at the user location at 141 may be immediately processed or stored for later processing and viewing. As described in U.S. Reissue Pat. 36,801 issued to James D. Logan et al. by the invention, the incoming broadcast programming may be concurrently viewed or otherwise processed while it is being recorded in a circular buffer for possible future use. A reserved portion of the storage unit seen at 143 may implement the circular buffer. This allows the user to utilize VCR-type controls to pause and selectively replay or process previously broadcast programming at different forward and reverse playback rates. With the pause capability, the system is constantly recording the last 5 minutes or so of a live radio broadcast, or the last 30 minutes or so of a live television broadcast. When the user hears or views a song or program that he or she likes, the user presses a "Catch" button, and the program will set aside the all of a predetermined part of the stored programming in the circular buffer, as well as a further predetermined part of the incoming broadcast that continues the saved portion, and retains both in temporary storage at 103. Later metadata may then be applied to that segment identifying the beginning and end of the program or song being played at the time the catch button was activated. If the button was hit after a program or song was over, but before or after another began, the system would assume the user was trying to capture the last played song.

Unless received in already parsed form from the remote location, the incoming broadcasts are parsed at 145 into segments that correspond to the segments created at the remote location at 105. As noted earlier, the available metadata may be used to subdivide the incoming broadcast signals into segments. For example, the metadata may identify incoming segments by source and by start and end times. Alternatively, the metadata may include "fingerprint" or "signature" signal pattern that can be compared with incoming broadcast signals to identify particular segments, and may further include timing information, which specifies the beginning and ending of each segment relative to the location of the unique signature.

After individual segments have been identified in the incoming broadcast stream at 145, they may be immediately processed or stored for future use in the storage unit 145. Not all of the segments that are identified may be of further use; accordingly, the available metadata may be used to select or discard particular segments as indicated at 151, and to process only the remaining segments, or selectively store them for future processing or playback at 153.

At 161, the selected segments may be modified or reorganized in a variety of ways in accordance with the metadata. For example, the sequence in which program segments are presented for playback may be modified, and programming materials not necessarily included in with the originally broadcast materials may be "spliced" into the presentation, or all or part of selected segments may be deleted from the presentation. The resulting program content which is in condition for playback may be immediately presented to the user, or it may be stored at 163 for selective playback at a more convenient time as indicated at 171 and 190.

As illustrated in FIG. 1 at 180 and 135, the user may create descriptive metadata and may edit metadata previously received or created in a variety of ways to personalize the storage, reorganization and playback of available broadcast programming.

It should be observed that the process of creating and editing metadata may be based on any one of the various versions of the received content; that is, the content as received and stored at 143, as parsed and stored at 147, as reduced to specific segments remaining after the selection and discarding process at 151, and as modified at 161 and stored for viewing at 163.

It is also important to note that the parsing, selection and modification processes may be performed at different times using, in each case, the most recently stored version of the programming content and the metadata that is available at that time. For example, metadata that is used to parse incoming segments at 145 may be made available from the parser 105 at the remote facility at an earlier time than descriptive metadata arrives from the remote creation process 111. The presence of the storage unit 143 allows received broadcasting signals to be held until parsing metadata arrives which will subdivide the received programming into logical units that can then be still later selected and modified with the aid of descriptive metadata that arrives only after it is created by the remote editing process. Note also that the metadata which arrives first to subdivide the programming stream into logical segments, as well as available metadata which describes those segments, facilitates the task at the user location of generating still further supplemental metadata which describes, rates, annotates or recommends programming content for other users.

In the description that follows, many of the features and functions summarized above and illustrated in FIG. 1 will be presented in more detail.

Program Source 100

The present invention contemplates the creation and use of metadata for describing and manipulating programming content of the type typically broadcast for public consumption by radio and television broadcast stations; disseminated by cable and satellite systems and, more recently, via the Internet; or published for general consumption on data storage media, such as DVD disks. This broadcast programming may be in analog or digital form and, in some instances, may be obtained from a content provider prior to being broadcast. It is important to observe that the "broadcast programming" from the source 100 is available for processing at both a remote station and at the user's location as illustrated in FIG. 1.

The principle illustrative embodiment as described below is used to select, organize, disseminate, store and reproduce television broadcast programming. It should be understood however that the principles of the invention are, with few exceptions, equally applicable to radio broadcast programming, to programming that is published via the Internet, and to programming such as movies which are transported to the user on published data storage media, such as DVD disks.

Storage Unit 103

While the parsing of programming content into segments and the association of descriptive metadata with those segments may be automated to some extent as described later, it is frequently desirable to provide one or more human-operated editing workstations which can used to adjust or "fine tune" the time position of markers which delimit the beginning and end positions of segments, and to manually compose descriptive metadata, provide qualitative rankings, and to otherwise classify or describe the content of each segment. The use of storage units 103 and/or 107 permits unparsed and parsed programming to be temporarily stored so that it may be processed through one or more multi-channel editing stations where a single operator can effectively insure the accuracy of the parsing process and the addition of descriptive metadata to plurality of concurrently received broadcast programming channels. These multi-channel editing stations are used at 106 and 111 to subdivide program content into segments described by metadata. The multichannel editing stations employ variable speed playback techniques to control the placement of time markers, and may display close caption text in an editing window to assist the human editor in composing descriptive metadata and classifying the content. These multichannel editing stations scan the programming content in storage units 103 and/or 105 and place the resulting metadata in the store 113 for distribution to users as discussed later.

Parsing Broadcast Programming at 105

Automated means may be used to subdivide programming into segments. For example, segment delimiters may be created in response to the detection of scene changes (frequently indicated by blank frames in TV content) or by abrupt changes in overall image content when backgrounds change. In addition, voice recognition processing may be used to detect and automatically map the times when particular individuals are speaking. Predetermined image content may be detected to identify repeatedly used screen displays at the beginning and end of programs, and at program breaks or intermissions. In the same way, audio recognition may be used to identify standard theme songs and announcements used at the beginning of certain program segments. When such standard elements also serve as program segment identifiers, they may be associated with standard descriptive metadata that is automatically accessed from a library and added to form all or part of the descriptive metadata that is associated with the identified segment.

Frequently, when parsing television programming, the audio and video components have different time boundaries. For example, if it were desired to subdivide a football game telecast on a play-by-play basis, the audio description may well begin before and extend well after the actual play as seen in the video component. If the programming was segmented based on the video alone, the audio would be segmented in a somewhat non-optimal fashion while, in the same way, isolating a video segment alone might cut speakers off in mid-sentence. This follows from the fact that commentary is not frequently not timed to occur between the beginning and end of the activities shown on the video portion of the program.

Thus, it would be advantageous at times to split the audio at a different point from the video. This strategy might result, however, in interrupting a commentary underway when the next visual segment began. As long as the audio structure does not match the video structure, the human editor should be provided with the ability to independently select different beginning and end points for the video and audio segments, and then be provided with mechanisms for shortening the longer of the two, or lengthening the shorter of the two. The audio content may be lengthened simply by adding one or more periods of silence to the audio stream, and may be shortened by deleting silent periods to compress the presentation. The video presentation can be lengthened by adding "filler content", by adding freeze-frame displays, or by reproducing content in slow motion.

Another strategy is to optimize the "smoothness" of the audio splits at the expense of the video splits. Thus, instead of splitting the video at the moment the ball is hiked, it might be split at a logical break point for the audio at some point before the ball is hiked. This might make the video a bit choppier, but audio smoother. Note that the image presentation can be more easily lengthened or shortened by slowing or speeding the display rate or by duplicating or deleting frames, whereas the human ear would easily detects the change in pitch when an attempt is made to alter the presentation rate of an audio signal.

Other method may be used to separate out the songs from the audio stream are by use signal analysis to distinguish music from talkover or to distinguish one song from another.

Another method used to determine a markup point which will eliminate song talkover is to estimate the likely spot of the end of talkover by employing a database that specifies how far into a song you must go before finding the lyrics or main theme of each song, or the point at the end of the song when the lyrics or main theme ends. This "start and end of music" point, would be used as a best guess as to when the DJ talkover stopped (or if at the end of the song, when the talkover was likely to start again). The DJs themselves often have this information and often use it as a guide that allows them to talk right up until the point that the music starts. For stations that continually employ talkover, putting markers at these predetermined start and end points would provide assurance that no talkover was played with the song.

It should be noted that segments are not necessarily the contiguous results of subdividing the original programming signal. Segments can be unique, or can overlap or be nested within other segments. Moreover, a segment is not necessarily a subpart of an individual program as broadcast. A segment may be a combined collection or sequence of such programs, may correspond precisely to a single program as broadcast, or may be only one part of a longer program. Importantly, segments may be organized into groups of other segments or programs, and can form a hierarchy of sections, chapters, sub-chapters, etc. Thus, a single metadata entity may be associated in a variety of ways with a plurality of segments, while other metadata entities may be associated with only one segment.

Storing Parsed Segments

The programming content that is stored in discrete segments at 107 need not be a direct reproduction of the incoming program signal. Redundancies and overlapping content may be advantageously removed. For example, when audio content is stored, the periods of silence may be removed for more compact storage. The content signal may also be compressed if desired using, for example, MPEG compression for video and MP3 compression for radio broadcast programming. A linear programming process may be used to allocate segments for the scarce viewing time allocated by the user.

After the continuous broadcast data has be assembled into individual segments, it is frequently preferable to store those segments so that the descriptive metadata which describes each segment can be created, automatically or by a human editor, or both, and be associated with the program content at a pace which is independent of rate at which the segments were originally broadcast. The nature of the descriptive metadata as thus created is described next.

Creating Metadata at 111

First, it should be noted that if the metadata is not positionally associated with the segments it describes by being imbedded with, or transmitted at the same time as, the content data, some of the metadata performs the function of identifying the associated program content.

Stored segments may be identified by a file name, a URL, or by some other unique access key (such as the primary key value in a relational database storage system). When segments can be identified and accessed when needed using such an access key, simply including that key value with the descriptive metadata suffices.

However, when metadata created at the remote location must be associated with program content received at the user location, a different mechanism is needed. As one approach, the program segment may be specified by the combination of an identifier which specifies a broadcast program source (e.g. a particular broadcasting station or cable channel) together with the start and ending times at which the particular programming segment was broadcast. These "time stamp" values are sent with the metadata to the user location and matched against time stamp information associated with the broadcast programming when received at the user station. For example, a TV program segment may be identified by data indicating the segment was broadcast by WGN beginning at 11:23:42 to 11:32:16 GMT on Oct. 12, 2000.

At times, predetermined time shifts occur when programs are distributed over cable facilities and the like. When that occurs, predetermined time offsets can be added to or subtracted from the values specified in the metadata, either before or after the metadata is transmitted to the user location. The magnitude of these standard offsets may be determined by detecting the time when predetermined signal patterns are received at the user location, comparing that time with the time when that signal pattern was broadcast as measured at the remote station to generate the offset value to be applied to all segments experiencing the same time shift as the predetermined signal pattern.

The technique of detecting predetermined signal patterns may be used to establish not only the timing but also the identity of a segment of a sequence of segments. For example, one or more a unique "signatures" may be extracted or derived from a sequence of programming segments from a particular source. The metadata for individual segments may then include values that specify a time offset from the signature marker and, in that way, uniquely identify the segment.

The technique of identifying segments by means of "signatures" may be used when the stream from which the metadata was derived differs from the stream recorded by the consumer. For instance, if a local broadcast changed the timing of a broadcast program in order to introduce advertising of different lengths, or to add locally focused content not included with the version from which the metadata is made, problems would arise. As another example, the metadata might describe segments within a pay-per-view movie that might be received at different times by different users. In this case, "signature" or "content-based time stamps" may be used to associate metadata with the stored content under these circumstances.

When the metadata is created, a "signal pattern," or "fingerprint" extracted or derived from the content is used to identify a known time position in the "parent" copy of the version from which the metadata is created. This fingerprint or pattern may also uniquely identify the parent copy, distinguishing it from other content. This fingerprint exists at a measurable time offset from an "index point" in the parent copy used to associate metadata with the content. For instance, if the metadata were marking the beginning of an advertising segment, the fingerprint should be within and near the start of that advertising segment. Alternatively, the fingerprint to be detected to establish the time mark may be within only the first of a sequence of segments, with the first and remaining segments having start and end times expressed by offsets from the single time mark.

Metadata used to subdivide programming content may take a variety of forms. It may specify the position of markers, which delimit individual segments within a programming sequence by, for example, specifying byte offsets in a file of digital programming data, or by specifying the time position relative to some reference time when segments begin or end.

Alternatively, metadata may specify identifiable signal characteristics or "signatures" within a programming signal stream. These signatures may be detected to establish the time or data position of markers that may then be used as a base reference for data or time offsets which delimit the programming into segments. Such identifiable signal characteristics may occur naturally within the programming (such as scene changes in a video signal indicated by blank frames, the appearance of a new voice or other detectable signal pattern, or periods of silence) or may be created by ancillary signals inserted into the program stream or in a parallel transmission to serve as markers. Such ancillary signaling may take the form of as identification tones, framing signals, digitally expressed data, and the like.

Using pattern-matching techniques, each piece of content stored at 103 or 143 may be compared to a specific fingerprint signature. When a match is found, segments occurring before or after the matching pattern may be identified at both the remote site where metadata is created and at the user location where metadata from the remote site is associated with the corresponding received broadcast segment. Multiple fingerprints may be used in order to continually synchronize the two versions.

The viewing habits of users as revealed by usage logs may be analyzed to subdivide programming into logical segments. With a large enough base of users, a profile of viewing could be constructed for a given program which would tend to indicate when users skipped particular segments, or used the mute control to silence a particular segments, and to further identify segments which held viewer's attention. This type of observed behavior could be combined with other techniques, such as blank frame, scene and voice change detection, and analysis of the closed caption text to further automatically determine the boundaries between logical segments.

The segment boundaries chosen by automated techniques may be refined by a human editor who makes adjustments to the timing of the automatically selected boundaries as needed. Thus using automated techniques, it is possible to subdivide broadcast programming into logical segments and to provide a figure of merit rating which can be sent to those who view the same programming on a delayed basis to assist them in making program viewing and recording selections, and, if desired, to automate those selections in whole or in part.

Storing Metadata at 113 and 133

As noted earlier, metadata describing the segments identified during the parsing process at 105 may be created at 111 in a variety of ways and stored at 113 for potential distribution to users. In addition, metadata created by users may be received via the communications facility 130 to supplement or replace the metadata created at 111.

Metadata created by users may be shared directly between users. When shareable metadata exists at a user location, it may be 'registered" by supplying its resource address (such as an Internet URL) to the remote location which then relays the URL to other users who directly access the descriptive metadata from the other user's metadata storage 133 in a peer-to-peer transfer. In this form, the remote facility shown in FIG. 1 operates as a registry or directory that permits users to share descriptive metadata about broadcast programming with one another on a community basis.

The remote facility may subdivide available broadcast programming into segments as previously described and then associate each segment with references or pointers to metadata created by users and hosted on user's computers or on an available storage resource (including, for example, storage space made available at 113 for storing metadata).

As an alternative, the metadata provided by users may include segment identification information. For example, a user may identify a segment of programming by marking its beginning and end, and then create metadata, which describes, rates or classifies that segment. Programming at the user location creates identification metadata for the segment using any of the techniques discussed earlier; for example, by extracting and transmitting a unique fingerprint from the identified programming and transmitting this fingerprint together with start and end offsets, or by identifying the programming source together with the time stamp information specifying the times at which the beginning and end of the segment were originally broadcast.

The user may review metadata supplied by other users and presented as a program guide to the available stored programming. Before the descriptive metadata from other users is displayed, the segment identification portion of the received metadata may be compared with the programming content stored at 143, 147, 153 or 163 (or with metadata stored at 133 which identifies the content available to the user). In this way, only that descriptive metadata from other users which describes available programming need be reviewed.

Alternatively, a viewer may transmit a request to the remote facility for additional information about a particular program (which may include multiple segments), or the preferences of the user as stored in 117 may be expressly stated by the user or derived from the user's viewing history. These requests and/or preferences stored at 117 may then be used at 115 to select desired metadata (including references to metadata stored elsewhere) in the store 113 for transmission to the requesting user.

Thus, the metadata which is created by created by and shared among users one or a combination of the following forms:

1. Qualitative (rankings, reviews, etc.);
2. Descriptive (summary, topics, etc.);

3. Segment identifications (start time, elapsed time, ending time, source, detectable characteristic, ancillary codes); and
4. Cross-references or pointers to metadata stored at addressable resource locations, including metadata created and hosted by other users.

Metadata that includes the URL of a World Wide Web resource provides a robust mechanism for associating the content of particular segments of broadcast programming to both additional information and related interactive transactions. For example, metadata may be associated with programming that permits viewers to learn more about or to purchase products or services related to the programming content. As described above, individual users may also create addressable resources, such as Web pages, and associate links to those resources with viewed programming segments. For example, a fan club for a particular actor might create a Web site devoted to that actor, and then share metadata containing the URL to that Web site with other viewers.

The user's ability to create and share metadata that describes, classifies or relates to selected broadcast programming segments thus enables users to create a community surrounding those segments in which a rich variety of information exchanges and transactions can occur. Users can, in effect, use the subject matter of broadcast programming as public bulletin board upon which to post comments about the program, ratings and descriptive data which can be used as a basis for indexing and retrieving program content, and for linking in related information from other sources, or for conducting a marketplace by posting offers to sell and to buy goods or services relating to or suggested by program content.

A "Community Markup" system (here called "CM") may be implemented that serves two purposes: it may be used as a way to develop markup data for sources of program information that may have an insufficiently large audience to justify the creation of markup by a commercial enterprise, or to improve the quantity or quality of markup data offered by commercial sources.

To optimize the benefit of the community markup, program guide data may be made available to potential users to identify what stations to record. As users can't go back after a broadcast and record it, this method would insure the maximum number of recorded copies will be available both for markup and playback with any CM effort.

CM can also be used to improve previously produced markup information. For example, if the markup does not accurately reflect the extent to which an announcer may have "talked over" a song, users will have editing tools available to them to alter the placement of the song delimiters and excise the talkover. The CM system will allow users to join a community whereby they will be able to upload their improved markups to a central server at 113 so that other users may access them. A "barter" system may be employed so that, when a user creates original markup data, he or she would then be entitled to receive markup data from other users, potentially avoiding the free-rider problem.

Improved markups may be downloaded and used to improve previously recorded songs or other content stored at 143, 147 or 153 in an automatic mode. Thus, even if several days elapse before the improved markup is available, the existing recording library would be automatically upgraded. This upgrading of the library would be performed transparently to the user.

As the originally recorded material is still in local storage, and only the metadata defining the playback markers is altered as a result of the new metadata, the recipient of community improved markup could always "undo" the automatic marker movement and restore the original recording and associated splits.

In cases where the system receives multiple markups, they can be averaged together for greater accuracy with outliers being deleted. This averaging function can be performed either at the server based on metadata received and stored at 113, or at the user location based on metadata received and stored at 133.

Note that community created markup would not necessarily have to be stored on a central server. Markup data can be stored solely on user machines and shared via peer-to-peer transfers (e. g. using an architecture of the type employed by Gnutella). In this environment, users would employ shared directory, which would identify metadata about a recording they had made, which exists in storage at 133 at another user location.

Community Markup (CM) may be created as a byproduct of the user's use of locally generated metadata for creating a personalized program library. For example, the user may record a lengthy radio broadcast from a favorite station and then selects particular songs for inclusion in a personal library, either by using markup signals provided by an remote markup source, or by using the available editing tools at 135, the songs which are identified may contain DJ talkover at the beginning or end of the song. In that case, the user may be employ a one-step-editing feature that permits the user to listen to a song and, when a transition occurs from talk to music, or visa versa, they can simply click on a "scissors" button which moves the start-point or end point of play, for that song, so that, the next time it's played, the new start and/or end point takes effect. Importantly, the talkover is not erased and the play marker is merely moved. If the user did not time very well the use of the scissors, he can hit an "undo" button and redo the clipping process.

At any time, the user may elect to share the locally stored markup signals with others by transferring that markup to the server for storage at 113 where it is combined with the markup produced by others for that station and time frame, or by transferring the markup to another user with a peer-to-peer transfer. In this way, not only is the markup shared which accurately identifies desirable programming, the markup also operates as a recommendation for that section and, when aggregated among many users, offers the ability to identify and share the "best of today's programming" on a particular station.

A mechanism related to the "scissors" function described above would enable a given program segment (e.g. song) to be "split out" from the original program recording. Because the available metadata may not accurately identify the precise beginning and end point of a given song, a predetermined duration of programming is included at both the beginning and end of each song as identified by the preliminary metadata. This extra time provides "running room" to make sure that every program has at least the entire rendition in it. Since this extra length could include material from the program segment behind or ahead of the segment being edited, the interstitial material in the nebulous space between songs is duplicated and added to both songs as defined by the metadata. The user may then user the editing means, including the "scissors" function noted above, to provide a final adjustment to the start and end time. When program segments are permanently stored in a selection library, the added material excluded by the final edit may nonetheless be retained at both the beginning and ending to preserve the ability to adjust the start and end points even after the selected program segment is persistently stored in the library.

Programming may be described, classified and rated using metadata formats. Standard rating systems have been widely promulgated using the World Wide Web Consortium (W3C) Platform for Internet Content Selection (PICSJ). The PICS specification enables labels (metadata) to be associated with content and was originally designed to help parents and teachers control what children access on the Internet, but also facilitates other uses for labels, including code signing and privacy. PICS labels, and other metadata, may be advantageously expressed using the W3C's Resource Description Framework (RDF) which integrates a variety of web-based metadata activities including sitemaps, content ratings, stream channel definitions, search engine data collection (web crawling), digital library collections, and distributed authoring, using XML as an interchange syntax. Details tutorial information and formal specifications for PICS and RDF are available on the World Wide Web at http://www.w3.org/pics/ and http://www.w3.org/RDF/ respectively.

Storing User Data at 117

Whether the metadata which relates to programming segments is created at the remote source or at one or more user locations, it is frequently desirable to organize or filter the metadata so that they user can more easily obtain the benefit of that metadata which best fits the needs or desires of the individual user.

One mechanism for limiting the amount of metadata actually presented to the user is to simply store all received metadata at 133 and then to employ means for sorting and/or indexing the stored metadata so that desired metadata can be located in response to the user's specifications. As an alternative, the user's specifications may be uploaded via the communications facility 130 and stored at 117 at the remote facility. The user's specifications or preferences as stored at 117 are then used at 115 to select only that metadata which best fits the user's needs for transmission to the user's metadata storage at 133.

The user's preferences may be derived from his or her activity. For example, the particular programs a user chooses to save or view may be monitored to determine the user apparent content preferences. Preference data may be produced at the user's location and stored with other metadata in the store 133, from which it may be used locally or sent to the remote location for use there. Alternatively, "user log" data recording the user's activity may be transmitted to the remote location where it is analyzed to produce preference data.

Metadata which is derived from an analysis of the recorded viewing or editing choices made by other viewers, which may be termed "implicit metadata," includes values such as: the number of users with whom the viewer had common tastes who watched a particular program, or metadata based on analyzing such events as (a) who surfed out of, or did not complete watching, a certain show, or never recorded it in the first place; (b) who took a certain amount of time to watch the recording (if it's a preferred program to a viewer, it will be viewed sooner; or (c) what percent of the program, on average, was skipped.

Once the preference data are determined, they may used in a variety of ways:

a). Preference data may be used at 151 to select or discard particular received broadcast segments so that only those which are more likely to be of interest to the user are saved, thus conserving storage space;

b). Preference data may be used at 161 to modify program content by, for example, inserting, interleaving or substituting advertising or other materials with received program materials based on the users interests;

c). Preference data may be used at 171 to assist the user in determining which received segments to play, either by automatically presenting those segments most likely to be of interest to the user, or by presenting a program guide containing or highlighting segments of interest from which the user makes the final program selection;

d). Preference data may be used to help the user select program segments which are made the subject of additional, user-created metadata which is then used locally (e.g. bookmarks or notes for the user's own use) or uploaded to the remote location or shared with other users as noted above;

e). Preference data may be used at the remote location where it is stored at 117 and used at 115 to select metadata for transmission to the user;

f). Preference data for individual users or combined preference data from many users may be used at 103, 107 and 113 to determine which programming content and descriptive metadata should be stored, and when previously stored content and metadata should be discarded, to make the most efficient use of limited storage space in light of user demand; and g). Preference data may be collected based on the usage of, or ratings supplied for, the metadata itself. In this way, users may rate the perceived value of metadata created automatically or by the editors at the remote facility (at 111) and this rating data may then be used at 115 to select not only programming of particular interest but also to select the metadata deemed to be of the most value.

Note that the metadata created at 111 and/or 180, and stored at 113 and/or 133, may include metadata used to display an electronic program guide (EPG) for the user which displays in some convenient format information concerning the content of available broadcast programming. Such displayed metadata associates items of descriptive information with one or more program segments. It is thus frequently advantageous to provide the user with means for associating user-created comments, notes, reviews, ratings, and the like by using the EPG display to identify and select the program segments with which the newly created metadata is associated. Metadata created in this way is thus readily shared with other users who share comparable EPG metadata by the simple mechanism of permitting a user to request additional information about a displayed program guide item.

As noted earlier, metadata created by individual users may be simply stored locally at 133 as an Internet accessible resource. Web crawling "spider" programs executing on remote computers may then retrieve and index this metadata and then act as "search engine" directories that may be publicly accessed to locate metadata of interest. For example, a search for "Stardust" might locate metadata describing an audio recording of the song by that name, biographic programming about the composer or performing artists, and the like. Thus, the descriptive metadata created by professional editors and/or users can form the basis for finding and enjoying content that would otherwise be difficult to index because of its non-textual character.

Metadata can be developed to characterize individual program segments by processing log file data representing choices made by users in selecting and/or abandoning programs, and from program ratings expressly provided by users. When aggregated by retrieving and combining such data from many users, and when further correlated with demographic data about the same users, rating information can be provided which tends to indicate what other viewers having similar backgrounds and similar past preferences preferred among the currently available program materials.

Ratings data compiled from actual user selections may provide unique information on how specific consumers react to specific songs at specific times. Thus, a recording studio might release a new single, and immediately thereafter determine how many listeners in a certain demographic had deleted, saved, or listened to that song multiple times. Express song rating data provided by users could be used in addition to or instead of implicit rating data to identify specific program segments that were well received or uniformly disliked.

When programming is broadcast in one geographic area before being broadcast in another, or when programming is repeated, the viewing and listening behavior of users exposed to the earlier broadcast can be used to provide rating information for later users. Thus, the habits of TV viewers on the east coast of the United States could be analyzed in advance of the later rebroadcast of the same programming on the west coast, so that ratings data tending to reflect which of the programs were preferred may be supplied to west coast viewers in advance. In addition, west coast viewers would have the benefit of advance reviews and summaries of programs created during the earlier broadcast. In the same way, any viewer using a personal video recorder (PVR) or other means for accessing program materials on a delayed basis could be aided in the selection of that program which they, as individuals, would be most likely to enjoy by the availability of rating and review metadata from earlier viewers having similar interests.

Content and Metadata Communications

The transfer of both content and metadata is illustrated at 130 in FIG. 1. As described here, both the remote location and the user location may receive and process programming signals (content) from a broadcast programming source. In addition, content may be sent from the remote location to the user location, and content may also be sent from the user location to the remote facility or to other users on a peer-to-peer basis. By whatever path is used, the content which is presented to users is made available to a large number of potential users, and the metadata which describes that programming material is created to aid those users (or particular users) to selectively record and view this programming material.

The metadata may be created at the remote facility and transferred on a selective basis to individual users, or it may be created by users and transferred to the remote facility for redistribution to other viewers, or it may be transmitted directly from user to user on a peer-to-peer basis.

The metadata may be transmitted with the programming content, or may be transmitted at a later time, or over a different communication pathway. In many program transmission systems, some of the available bandwidth is allocated to metadata, as typified by program guide channels or time slots provided by the vertical blanking interval (VBI) in a television signal. These existing pathways may be used to transfer the metadata contemplated by the present invention which contemplates, in many implementations, the transfer of metadata after the programming material has been broadcast but before the programming material is viewed on a delayed or time-shifted basis after having been recorded earlier.

Thus, as described here, the metadata may be created by editors or viewers who comment on or rate viewed material at the time of or after its initial broadcast, with the metadata being transferred to end users to facilitate the selection, recording and playback of desired material on a time shifted basis. In summary, the metadata flow need not be transmitted before or concurrently with the original broadcast, but is may be created by early viewers and used by later viewers who watch the programming on a delayed basis, either because the version they watch was broadcast later or because the version they watch was previously recorded for later viewing.

Creating and Editing Metadata at the User Location

As previously noted, metadata may be both created (at 180) and edited (at 135) at the user location. The user may programmatically derive this locally created metadata from the viewing choices made without requiring any additional effort by the user, or the locally created metadata may be the result of interactive choices made by the viewer. For example, a viewer may receive metadata from the remote source which takes the form of an electronic program guide describing broadcast programming, and with respect to each item of such programming, the locally generated metadata may indicate whether or not given program segments had been (a) selected for storage for potential later showing, (b) selected for actual viewing, (c) viewed for a specified period before being terminated, (d) saved for later repeat viewing after having been viewed, (e) expressly rated by the viewer, or (f) made the subject of a written text review. This locally generated metadata reflecting the user's use of or assessment of the programming materials, as placed in storage unit 133, is then uploaded to a remote processing site for distribution to other viewers or simply placed in an addressable location from which it may be retrieved for processing by one or more rating services or by other viewers.

When the user stores broadcast programming in the store 143, the user has no control over the incoming content. To more easily control what is saved for possible future playback, the user may be provided with a "Never Again" button. Whenever the user is listening to or editing a program segment, such a song, or has highlighted that program in a library program listing, the user may press the Never Again button to prevent that song from being recorded or, if recorded, to automatically prevent that song from being presented to the user in a list of available songs. Alternatively, pressing the Never Again button may also permit the user to prohibit the listing of any song by a particular artist, of a particular song by any artist, or further editions of a serialized program.

Over time, the use of the Never Again button may be used to develop a "negative screen" of preferences for that user and may be used to automatically eliminate or reduce the number of program segments or songs related to a program song excluded by the Never Again button. The Never Again button may also be one of the several ways that users will be able to accumulate preference information that can be used to control playlists transmitted from the server or created locally by the user. Note that, like other metadata, the Never Again list is kept as a separate file and users may undo a Never Again designation at any time so that it will have no further effect on existing or future recorded content.

Instead of a negative filter, a huntlist, or "positive" filter may be used as well. With a huntlist, a user identifies which songs or which artists he wants the system to capture. In addition, a huntlist may contain "songbots" (algorithms that search for described types of songs that the user wishes to have captured). A typical songbot could be "All Top 40's from the '70's". Other huntlists may be created using collaborative filtering techniques. Huntlists may be compared with metadata developed at a remote server (with the comparison occurring at either the server or the user location) to flag desired songs as they arrive from the broadcast source and are stored at 143, or they may be used a sieve, whereby hunted songs are saved and non-hunted are deleted and never presented to the user. When songs are "found" by a huntlist created at a remote server, an email may be generated telling the user that new songs are now in the jukebox. When the huntlist operates locally, a dialog box or the like may be used to alert the user to the presence of the desired song or program segment. In addition, the user may access his huntlist and see through a visual cueing of some kind (different colors for instance) which songs have been captured and which have not.

The huntlist may be compared with metadata describing the programming broadcast by a plurality of different stations to identify stations and times when desired programming is most likely to occur, and a program controlled tuner may then be used to automatically capture broadcast content from the identified stations at the identified times. When program segments or songs identified on a huntlist are available for purchase, a "Buy" button or a "Sample" button, which allows a user to hear a sample of a song, may be presented to the user to enable the purchase to be evaluated and executed if desired.

Automatically Bookmarking Programming Content

The system contemplated by the present invention may further include a mechanism at 180 for automatically defining and generating bookmarks which may be applied to the content stored at 147, 153, and/or 163 to facilitating navigation of the stored content and/or for personalizing content as performed at 151, 161 and/or 171 to thereby selectively control the playback of programming materials at 190.

The leading objectives of the automatic bookmarking mechanism contemplated by this aspect of the present invention are to:

1. Automatically specify segment start and stop delimiter positions (at 145);
2. Automatically categorize the segments;
3. Automatically create descriptors for the segments;
4. Automatically eliminate redundancies if necessary at 151 and/or 171; and
5. Automatically concatenate related pieces of a story at 151, 161 and/or 171 to implement one or more different ways to watch television Content that is well suited for these bookmarking techniques consists of segment-able programming like news, sports, or shopping programming, but some techniques apply to other types of programming as well. The automatic bookmarking mechanism may be implemented with a variety of available technologies, including natural language processing, voice recognition, face recognition, sound recognition, and probability theory.

The bookmarking system can operate on the client side as noted above, or at 111 at the central facility (which can include at the broadcaster's facility) to create bookmarking metadata that may thereafter be downloaded to the client with the program (if the analysis work is done ahead of time) or via a separate channel such as the Internet. The bookmarking metadata may be created ahead of time before broadcast, or more likely, after the broadcast when there is a short window of time to create metadata before the viewer watches time-shifted material.

Creating Bookmarks from Close-Captioned Text

The preferred system may make extensive use of the closed-captioned text. The close caption text will be feed into a Natural Language Processing Engine (NLPE) in order to interpret the meaning of the material. When the system determines a change in topic, a marker is set. The system will also attempt to categorize the material and generate a short "slug" describing the material.

The closed caption material is typically fed into the NLPE system in blocks, as the system can process the material faster than it is broadcast. As a topic break might lie close to a break between blocks, the system processes overlapping blocks as needed to be sure no breaks came between, or close to the endpoint of a block. The close caption text, when fed through the NLPE, may also be used to generate a caption for each individual segment as well as to categorize the segment.

Closed captioning can be done live or ahead of time. When done ahead of time, it is synchronized quite tightly, within a fraction of a second, with the program content. For live captioning, tight synchronization is not typical, and the delay can be on the order of a few seconds. When loosely synchronized caption exists, the system may automatically attempt to re-synch the captioning with the video after recording. One way to do this would be just to use some measure of average delay for that type of content and adjust the captioning accordingly. A better method employs face recognition or shape recognition to analyze the video content to determine when a person is speaking by focusing on lip movements. The captioning could be re-timed to match up with the end of a speaker's as often as needed. Alternative, voice recognition could also be used when the captioning reflects the spoken sound track. Note that the accuracy of the voice recognition would not have to be very high since, if a definitive match was found every few words, the time delay could be re-adjusted until a subsequent match is found.

The bookmarking mechanism may use speech recognition in combination with a database of navigational words that commonly indicate that a break or segue is in process. These would include words or phrases such as "coming up next", "next week", "Over to you, Bill", etc. "When we return" would signal the start of an ad. Questions might often indicate a change in direction of the content. When such a phrase was located, a marker would be generated. Alternatively, the closed caption text may be scanned, or using voice recognition software may be used to process recorded speech, to find these words and phrases.

The manner in which users view a given program may be monitored to position automatically generated bookmarks. The video playback system typically includes a fast-forward mechanism that permits a user to rapidly search through a program until a passage of particular interest starts, at which time the user returns the player to normal viewing speed. Typically, the image can be seen during this movement and sometimes the audio can be heard as well, particularly if it is time-scaled to give the audio pitch control. This fast forwarding activity may be monitored to identify the beginning point of a segment of interest. The system is preferably able to collect and aggregate such bookmark position data on an anonymous basis, perhaps just from a minority of the total users, to identify the points in each piece of content where users frequently resume normal playback speed after fast-forwarding to a desired position. Note that, in general, the important bookmark to get right is the beginning of a segment. The end of a segment normally takes care of itself as people often skip out before getting to the end, or if not, the end of one segment becomes the beginning of another. The point is that few viewers fast forward to end a given passage, but rather fast forward through a segment or sequence of segments until the beginning of the next desired segment is reached. Due to this fact, time scaling is a useful tool for finding segment beginnings. This is because some number of users will scale forward rapidly, still understanding most of what is being said if the audio is able to be heard, or will be able to view a fast motion version of video programming, and will then slow down when the interesting material starts to play. It is this inflection point we are looking for. It will indicate a change in interest level to most viewers and thus could serve as a source of auto generated bookmarks. The preferred system accordingly aggregates time scaling commands from a large number of different viewers to deduce segment beginnings as an average of a concentrated group of these fast-to-normal transition times.

Viewers will typically overshoot the actual beginning of the next segment as they cannot discern that a new segment has started until they watch or listen to a bit of it. Some percentage of viewers may go back and try to start at the exact beginning, at least for some segments. As a result, the best way to fine-tune the estimate of the location of the segment beginning point would be to estimate the average overshooting error and subtract that distance from the deduced segment based on the average or calculated segment beginning. This average-error-length could be found through empirical study, or deduced, by again, monitoring viewer behavior on the system and watch that small number of viewers who go back and rewind to get to the exact beginning of a segment. In general, the system described by this invention would wish to err on the side of starting the segment too early as opposed to starting within the segment.

Since large numbers of people fast-forward through ads at high speeds, aggregating the data around these clusters (dropping out users who are obviously fast-forwarding past the ad itself) would give a good indication of where the ad stopped. Since the average user stops a certain number of seconds after the ad ends, this average stop time, minus the average error, could be used to deduce the end of the ad and start of the next segment.

By the same token, the aggregation of data which distinguishes program segments which are frequently skipped by fast forwarding from those that are viewed normally can be used to identify popular segments. For example, a substantial number of viewers may fast forward through the Tonight Show to find the Top Ten segment. The system can learn to spot these clusters of segments or content through which other viewers have fast-forwarded, label them and pass them on to other users allowing them to skip over these unwanted segments instead of fast-forwarding through them.

In particular, Hot Spots would be most interesting if the comparative group was matched the profile and preferences of the viewer. This would give it more of a collaborative filtering capability.

Another form of metadata that could be automatically generated from other viewers' actions is which segments elicited an interaction by other viewers of iTV functions. These might include an interaction with a Wink-like system whereby sport statistics are available over the data channel of the cable operator. For instance, a viewer might wish to focus on segments in a History Channel program where other viewers had accessed background information. Another example involves t-commerce and systems that allow viewers to purchases an item from the TV using the remote. In a home shopping channel, this sort of metadata could serve to guide a user to the hottest items to buy.

Sound Cues

For purposes of this section, it is useful to define a new type of content here called "rolling content." Whereas segmentable content includes news and weather and linear content includes shows like "Friends" and movies like "Gladiator," rolling content would include programming such as a soccer or hockey game, which is a hybrid. Programming with rolling content have periods of higher and lower interest, and some climaxes like goals, but the "breaks" are more analog in nature. Many cues indicative of a break in rolling content could be deduced by sophisticated audio recognition. Important sound recognition types would include laughter, applause, referee whistles, and crowd noise. Crowd noise for instance increases dramatically every time a home run is hit, or a shot on goal is taken in a soccer game. The system could understand how long it takes on average to develop a play in soccer that would cause a cheer and drop a marker in several seconds before each instance. In a comedy program like the David Letterman show, the "action" is expected to be continuous, so a marker would be dropped in after each instance of laughter, presuming that is the beginning of the next joke. A software algorithm might detect other types of sound information such as the level of excitement in a speaker's voice, or the quickness of speech. These variations could be transformed into bookmarks. Different algorithms could be developed for each type of sound, and vary by each show. The user could do further modification of the algorithms, for instance, deciding to watch 10 seconds rather than 30 seconds of content leading up to a crowd's roar. Alternatively, the system might "learn" preferences such as this by monitoring the specific user's use of the fast forward button or time scaling feature.

Recognizing Repeating Patterns

Multiple copies of the same show may be analyzed to see if patterns repeat themselves. These patterns might be in the video or audio and might signal the beginning of a segment. For instance, the appearance of the weather map might indicate the beginning of the weather report. The system would look for pattern markers that were spaced apart about the length of an expected segment. As stated earlier, the time scaling or fast-forward usage information could be used to confirm that these bookmarks are usable. In addition, if nobody is skipping forward to them, that tends to indicate they might not be correct.

Music Recognition

A music discriminator, that is a signal analyzer able to discriminate between music and talk and deduce when music is playing in the background, can be used to provide bookmarks. Music analysis may also be used to distinguish one type of music from another, and perhaps distinguish bands or songs. These algorithms could be useful for detecting breaks in a video show, as well. This technique could be particularly useful for detecting ads as many start with music.

For rolling content or linear content, detecting the type of music playing might be useful. In many cases, music is used to highlight the "essence" of a movie. In many movies, a characteristic type of music played during each action scene or love scene, for instance. Metadata based on the type and location of this background music could be used to classify areas of content into different moods or types of content such as love scenes, action scenes, etc. A user could use this information to just play back these portions of the content.

Another form of similar metadata would be the frequency of scene changes. More scene changes would indicate more action. By the same token, the degree of motion in the image itself can be detected from the amount of redundant information that is dropped out in the encoding process. This information could be used to deduce or measure the degree of motion in the scene, information which could be used to deduce the "action level" in the scene, perhaps in conjunction with other indicators.

Character Changes

The preferred system would be able to detect the coming and going of characters, announcers, or actors in the programming. This could be done through face recognition technology or through voice recognition (where different peoples' voices are recognized regardless of what they are saying). In news shows, this would be particularly useful when one announcer hands off to another. For other types of programming it might help to automate our "Favorites" Way to Watch (which we typically describe as a way to track Tiger Woods through a golf tournament). Further logic, implemented using data generated from voice or face recognition, may be used to determine who was the anchor and who were the subsidiary reporters. The breakpoints could be focused on the times where the camera went back to the main announcer.

Visual Cues

Scene recognition (as opposed to scene change recognition) would be useful in deducing breakpoints. Similar to sound recognition, visual recognition could (either now or in the future) spot when two newscasters were using a split screen, when stock prices were on the screen, when a ball went into the basket, etc. Overall visual metrics, such as the amount of movement on a soccer field, could be indicative of a timeout or frantic action.

User-Generated Bookmarks

Another form of non-tagging-station-generated bookmarks would be for users to create their own bookmarks by clicking a button as they watched the programming. This could be related to the Save feature (see below), or merely to enjoy while re-watching the programming. The user could also have the option to categorize and label the segment if both beginning and end points were denoted. If enough users in the monitored sampled bookmarked the same scene, the system could average these locations out to present a definitive mark to other users. In the same way, when a user bookmarks a spot in order to save a segment, this new viewer-generated location data could be used to create the deduced bookmark.

There are four types of viewer-generated bookmarking information: Fast-forwarding or other analog motions through the video, bookmarking for later repeat viewing or showing to others, bookmarks made to send to a friend, and bookmarks made for purposes of saving. In this list, viewers can be assumed to have the most thought into the actions later in the list. Viewers saving segments would therefore be presumed to have put the most thought into the exact placement of the bookmark. As a result, as data from these multiple sources is compiled and synthesized, extra weight would be put into the latter categories. The exact weightings could be tested through empirical testing. That is, an editor could study the video and determine the "proper" bookmark locations and then develop a model for using these data inputs in the most accurate fashion.

Note that once "deduced bookmarks" start to be presented to viewers, the system would cease to collect as much new information as viewers' navigation actions would then be based on the data being supplied. Therefore, the system would have to decide at what point enough field data had been collected before dispersing its deduced bookmarks.

Once deduced bookmarks were distributed to viewers, the system would monitor their usage. If some minimal number of viewers jumped to the given deduced bookmark but then shortly thereafter fast-forwarded a short distance, or rewound a short distance, this would be interpreted by the system as an attempt to adjust the bookmark. This adjustment distance would then be used to re-adjust the distributed bookmark going to viewers for the first time, as well as used to re-adjust bookmarks that were "in the field", that is already distributed. Again, data coming from viewers known to be "careful adjusters" would be given extra weight.

Certain viewers might be determined to have better skills in determining accurate skip points. This might be determined by looking at how well their marks clustered around the average location for a given markup point. The markup points offered by these users could then be given extra weight in the overall averaging process.

The averaging process could take into account multiple inputs—viewers' fast-forward stopping points, viewer-generated bookmarks, viewer-created segments that were saved, viewer adjustments, etc.

Aggregate User Feedback Used to Edit Breakpoints

Above we discussed how break points could be deduced by watching user's actions from which we could deduce breakpoints. Another way to use aggregated data is to watch how viewers use our proposed bookmarks. For instance, take the case of generating a break mark when the news announcer changes. This may not be the signal of a new story—it may just be the anchor handing off to a field person for a report. We could deduce that by watching how early users of the metadata don't skip at that break point, but watch the preceding section and go right on through this supposed next segment. If it were truly a break in the content, some percentage of people would be assumed to skip at that point or close to it. Therefore, if a bookmark is not used by some minimal percentage of people (who have watched the entire previous segment) as a launch pad to jump forward from, it would be assumed to not be a meaningful break. If no one uses a bookmark, then by definition it is not useful.

Correspondingly, if a high enough percentage of viewers skip out of the previous segment and then shortly skip out of this second segment, it could be assumed that the content is too similar and again, it is not a meaningful segment marker. Again, by definition, if there is an extremely high correlation between viewers skipping one section and then the second, the two are probably very closely linked and probably the same segment.

The exact percentages needed to make these decisions can be empirically tested as stated above.

But in general, the system can be organic and self-correcting. For instance, field data can always be used to second-guess a decision made by the system. If the system for instance, erases a marker, and then sees monitored viewers starting to fast-forward through material demarcated by the old erased marker, it can re-insert the marker.

Combining Different Metadata Using Bayesian Statistics

The NLPE will not always accurately segment the show. As such, it will be useful to combine this technique with others. Each technique will add additional information in determining the probability of a break. For instance, scene change analysis will be used to deduce when a scene occurs. If such a change occurs close to where the close caption analysis suggests there may be a topic change, then Bayesian statistical modeling will be used to predict the probability of a break.

Time-Based Data

Further data to add to the Bayesian analysis would include the time duration since the last break. Each program could have stored a frequency distribution of how often a topic change occurred. As the time-since-the-last-break increased towards, and then past, the average length of a segment, it increases the probability that an inference of a topic break is, in actuality, a real break. This time-based data would be added to the data synthesized by the Bayesian tool.

In other words, it's unlikely that CNN News would have a 10-second story. So the time-length factor would sharply mitigate the probability of the system producing a break after ten seconds even if the closed caption text and scene change analysis suggest such. On the other hand, segments rarely go past 2 minutes. So as the length of a segment approached a long duration, the "benefit of the doubt" would start to swing towards designating a break. Bayesian statistics is the methodology of revising probabilities based on new data.

Double-Indexing

Another goal of the system would be to develop two levels of bookmarking—one equivalent to chapters and one equivalent to paragraphs. The methods discussed above could all be adapted to determining minor changes from large ones.

By the same token, the system could produce "hard" bookmarks (ones it is confident in) and "soft" bookmarks. An interface could be offered whereby viewers could be offered a choice of being very careful in their surfing by jumping through all the soft bookmarks, or a bit more relaxed and only deal with hard ones.

Training

The system could be trained to adaptively produce (better) auto-generated bookmarks, by looking, over time, for correlation between known accurate segment markers (generated by hand or other accurate means) and those deduced though the means discussed above. The knowledge gained in this learning process would be used to update the Bayesian probabilities.

System-Created Text

NLPEs can identify key words in the text. These could be assembled to form very cryptic slugs that would fit on a TV screen. They might form a sentence if there was room on the display (George Bush in China), or the slug might just be a list of key words (Bush China). The screen display could be set up so that the user could hit the right button once at a particular slug to see a sentence that scrolled off the screen, or could hit a button to access a longer descriptive piece about a story.

Abbreviations: The system would keep a large library of common abbreviations and use these when needed in the slugs or other descriptive text to save space. This feature could be turned on or off by the user. Locating the cursor on an abbreviated word, and selecting it, would present the whole word. Alternatively, a viewer could go to an index of abbreviations.

Auto-generated bookmarks could be created on a customized basis for each viewer. Some of this computation could be done on the client or the customization could occur by customizing the presentation of bookmarks created by a central system.

Preference setting by each viewer would customize the presentation in a number of ways. The user could input levels of "hardness", the density of bookmarks, and the maximum or minimum length of segments desired. The viewer might also be aware of the level of "maturity" of bookmarks—that is the number of previous viewers upon which the deduced bookmarks are based. Have the bookmarks stopped "moving"? The viewer could also input keywords that would signify extra interest.

Alternatively, the system could deduce these parameters (desired density, for instance) or keywords on a viewer-by-viewer basis. If a user continually skipped out of a segment shortly after landing each time, the system might deduce that the user was not that interested in the content and therefore reduce the density of presented bookmarks.

If the system deduced a keyword for a user, it could then find the closest bookmark with which to demarcate it. For instance, if a keyword is found, the system might lower its threshold of tolerance for creating a bookmark thus allowing one to appear shortly before the word. In this manner if the user is surfing rapidly through the content, they will be sure to catch that segment close to the relevant point. The keyword could be displayed on the screen as well. These bookmark parameters could be displayed to viewers as they watched as visual icons on the periphery of the screen. In this way, viewers would be reminded of the information with which they could be navigating. It would also teach viewers what the unseen metadata was and encourage its use. Viewers would also be made aware of whether they were navigating with NLPE-derived markups or behavior-based deduced bookmarks.

User-Controlled Settings

Errors. An NLPE will never do a perfect job. It will sometimes generate markups that shouldn't be there (false positives) and at other times, miss breaks that do should be there (false negatives). Some users might have a preference for one or the other type of error. As such, viewers could have the option of setting a control that modulates the Bayesian statistical analysis tool such that one type of error or another was favored. (It is a bit of a zero-sum-game—trying to minimize one type of error will increase occurrences of the other.)

User Selectable Lead Ins.

Errors will also be made in finding the exact beginning and ends of segments. If the system tries to hit the spot exactly, it might often cut off some of pertinent material. This could be annoying and make the viewer have to scroll back to find the true beginning. Consequently, and end-marking bookmark may be delayed to add extra material to each identified just to "be on the long side". We envision having the user be able to modulate this type of error trade-off as well, as discussed above for marker error.

User Selectable Segment Types. The preferred system would let users indicate preferences for certain segment types. For instance, a sports fan might indicate a preference for jump balls (recognized by a whistle and characteristic picture composition), or applause lines on the Letterman show. This preference information is more form-based than content-based, the usual parameter used for personalizing.

Using Bookmarks

Save Button. With this button, a user could take a segment associated with a bookmark (e.g., the programming between one bookmark and the next) as stored at 151 and drop it into a "scrapbook" or vault at 153. This scrapbook could have a specific amount of storage space at 153 allocated to it. This storage space might be actual hard drive space on a viewer's PVR or shared storage on a network. In the case of the shared storage, the viewer's "ownership" of the stored content would indicated by metadata that associated that network-stored content with that viewer. Items dropped into the space could be assigned permanent or temporary storage. By default, segments would be sorted by, and assigned a label from, the show from which they came. The user could tag the segment with additional tag via voice input, a keyboard, or by selecting from a menu. (Each show would have menus of clip-types that made sense for that show— pass plays, tackles, runs, etc. for football). The segments in the scrapbook could be sorted by category bucket and or segment type. In addition, a user-operated "Scissors" tool could be used to clip off unwanted content. Playlists could be setup and segments could be sorted by type or by time, etc. Furthermore, the video scrapbook could be implemented by having the users do both cuts to define the segment. In this way, they won't rely on metadata to automatically copy the piece out of the stream, although they could use the metadata to navigate to the desired point at which to cut.

Scanning Playback. One playback tool that is not necessarily associated with automated markup may be thought of as a "scan mode," similar to that found in radios. In radios, scan will jump from channel to channel, giving you a sample of each. In an equivalent PVR feature, the TV could play short segments of each segment and then go to the next one if the viewer doesn't hit a Play button. This feature would be best applied where the chance of the user wanting to see a particular piece is low and it's too tedious to keep hitting the Next button.

"Sweet Spot" Surfing. A NLPE would be able to find the heart of a story. Currently this technology is used to summarize a newspaper article for instance. In our application, the NLPE would identify the key segment of a news story or other segment. This would be the "sweet spot" of a segment. Our editors could also demarcate these sweet spots. Alternatively, they could be deduced by watching where our viewers put their systems into slow motion, or replayed the content. Sweet spot surfing could be a way to let users get right to the juicy part of each segment, without necessarily starting at the very beginning of the logical segment. It could be the spot that a viewer jumped to when hitting the Next button or employing the Scan button (see below).

Sweet spots could also be deduced by analyzing navigation patterns produced by other viewers. These would be the portions of segments never fast-forwarded. In this model of sweet-spot surfing, the system would set the bookmark at the beginning of this section and let viewers land right in the middle of the larger section.

Segment Filters. The idea here is to treat ads or other repeatable segments of content as recordable scrapbook items. These segments could be fingerprinted and have a duration associated with them. When the PVR spotted an ad or other particular type of repeated segment, it would back up to the beginning of the segment and go to the end and demarcate the segment. These bookmarks could be loaded into the system for viewer use.

These segments could also be treated through a rules-based system assuming that they are ads. For instance, the rules might say that any ad that the viewer has seen "X" number of times, be deleted, or automatically skipped on playback, etc. In some cases, for instance with an ad-supported modality, the user might have to watch a segment of it before being allowed to continue on.

Features similar to Never Again and the Huntlist described in the above-identified previously filed applications could be set up. The Never Again feature is a personalized list of segments, which the user does not wish to see again. This list can be stored on the client or on the network. The user could add a segment to the list during viewing by a command or could construct the list during a non-viewing session. The Huntlist is a similar sort of list, personalized by viewer and constructed in a similar manner. In this case, however, an item on the Huntlist would be given special status and highlighted in certain ways to bring it to the attention of the viewer. It could even be automatically saved for that viewer. The user would go to a database and request the system pull down Budweiser ads. Our system would then download fingerprints for those ads to the client PVR to be used to hunt for the relevant clips.

Other ways to identify ads would be to look for scrolling text, 800 numbers, and abrupt change in the frequency of scene changes. In other cases, the "scene format" may suddenly go away. For instance, the Fox scoreboard in the upper left, or part of the Bloomberg information matrix may go away to make room for the ad. If it were a baseball game, scene recognition techniques could use a database of shots of infields, hitters, etc. to detect that the game was still showing. If it is a news show, there may not be a talking head in the picture. A database of newscaster facial images or voices could be maintained for each show, and if someone not from the list is deemed to be present, this fact could indicate an ad. Similarly, a database of products commonly advertised, may be maintained and used to determine if advertising was being viewed or not. In addition, an algorithm detecting the excitement level in a voice or other tonal quality might indicate it was not a newscaster, or even an interviewee. Ads might also have people speaking quicker. And currently, a lot of ads don't have closed caption text. Any number of these clues may be used in combination with Bayesian techniques to determine the probability of an ad break.

Note, that some clues posit the location of a break point (switching of speakers, for instance) without knowing if there is a change in subject matter, whereas other clues indicate the presence of an ad (mention of a product name, for instance) without knowing where the break is. By combining both types of information, the content may be both segmented and categorized. This technique of combining content information with segmenting clues may be used for other types of content besides ads.

Reminder System. An NLPE could also detect when a station was promoting future items, segments, or stories. "Next week, we'll be looking at", would be one example. When these were detected, the user could be presented with an option of having a reminder sent to him to watch it. For live viewing, a reminder could be sent via email or displayed on the TV at some time before or during the playing of this segment (or the show itself as the promotion by the station probably wouldn't specify the exact time during the show). Alternatively, the system could automatically record the upcoming show. It would bookmark the show segment if it could be located by text analysis and display a reminder that it had been recorded and located on a program guide.

Sharing Locally Created or Edited Metadata with Other Users

Note that, when metadata is placed in an addressable location, other users may retrieve it on a peer-to-peer basis. In this arrangement, a user might be simply supplied with a list of URLs at which other users having similar backgrounds, or viewers who were known and trusted, could post reviewable metadata. In this way, a user could affirmatively recommend certain programming and affirmatively discourage other users from viewing other programming.

Similarly, one user could bookmark an individual program or a segment of a program, associate a recommendation or comment with the bookmarked content, and make the program or program segment identification data and the comment or recommendation available to a special interest group or to a specific individual. In order to distribute metadata to designated users, it may be structured to include addressee data which specifies individuals or groups, so that bookmarking metadata of this kind can be affirmatively pushed to targeted users, or pulled by users who request metadata contributed for their specific attention, or for the attention of a group to which they belong.

Using the facilities of an interactive digital cable television networks, a viewer could be watching a show live and want to recommend it to another friend. Using a remote control, the user could select one or more friends from a preset displayed list and then transmit to those designated persons a "watch this" message that might be displayed as close-captioned text on the friend's screen. Properly programmed, the receiver could provide the option to open a window on the TV screen for a PIP ("picture-in-picture") display of the recommended show. Alternatively, using the Internet, a message could be sent via an instant bookmarking messaging connection or by email to a designated person or persons.

Bookmarking metadata might also be transmitted to programmable VCRs and digital PVRs to automatically initiate the recording of designated programs or program segments while, at the same time, advisory messages from the metadata sender to the target viewer could be sent to notify the recipient that selected programming had been recorded for their benefit. Such a system for remotely controlling a designated receiver would include a security firewall so that only authorized senders would be able to access and program the recorder. In addition, when recording space was limited on the target recorder, an appropriate algorithm would be used to prioritize the importance of someone else's recording suggestion so that important existing recordings were not overwritten and space was conserved for future programming having a higher priority.

Note that the use of such a "Watch This" bookmark messaging facility is not limited to live broadcast material. Through the use of a predetermined program identification system, either based on a source-plus-broadcast-time identifier, or a unique program identifier, or a signature-plus-time-offset designation, someone viewing a previously recorded program could also send a bookmarking message to one or more persons recommending content which may (or may not) be available to the recipient either in recorded form or in a future broadcast. The receiver of these recommendations would have the option to forego privacy and permit the message sender to access metadata (e.g. at 133 in FIG. 1) to determine in advance whether the recommended programming was available to the recipient.

Metadata in the store 133 at the user's location which identifies previously recorded and locally available programming content (in one or more of the content storage units 143, 147, 153 or 163) may be transmitted to the user data store 117 at the remote location to select descriptive metadata at 115 from the metadata store 113. In this way, recommendations, ratings, descriptive EPG data, and the like from both professional reviewers and from other viewers may be returned to the user as an aid to selecting programming content of interest from the available recorded materials.

When "watch this" messages of the type described above are relayed to recipients via a remote resource, they may be combined to form aggregate recommendation data, enabling any viewer to identify programming that has been most frequently recommended to others.

Although the present invention contemplates that metadata which is created at one location and made available to another location and further that this metadata relates to broadcast programming content that is independently available at both locations. Where appropriate, when content available at the location where the metadata is created is not already available at a destination location, it may be transmitted with the metadata. For example, locally created content (such as home video recordings) may be stored at the user location, described by metadata, and both the content and the metadata may be distributed. In addition, program content providers may authorize the redistribution of their content under appropriate conditions (for example, under the condition that the advertising is not deleted), in which case both the content and the metadata which was obtained from another source, or metadata created locally by a viewer, may be made available to other users. In one preferred mode, metadata stored at 133 and published by a user through a central server location or by a direct peer-to-peer connection may include the URL or identifier of the program content which may be retrieved by another user who selects in by first displaying its descriptive metadata.

Storing Content at 102, 107, 143, 147, 153 and 163

As previously noted, content programming is initially stored at 143 in a mass storage unit that may also serve as a circular buffer store to enable the user to pause, replay, and fast forward within a predetermined duration of recently received incoming broadcast programming. By using the local edit controls at 136, the user can employ metadata to identify selected program segments for inclusion in a program playback library. Metadata created by the user or the remote server, or signal processing techniques, may be used to parse the program content as broadcast into segments at 145, and further metadata may be used to select, discard or modify the programming content at 151, 161 and 171 before it is reproduced.

It should be noted that the storage units shown at 143, 147, 153 and 163 in FIG. 1 are "logical" storage units, which can be, and normally should be, implemented by single physical device or group of devices. During use, actual copies of program segments need not be copied from one logical storage location to another. Instead, the contents of the logical or "virtual" storage units 147, 153 and 163 may be defined by metadata which describes and provides pointers two program segments which are a subset of the program content stored in the "inbox storage" unit 143. Only some of the parsed program segments identified by metadata in the logical parsed segment storage unit 147 are selected for potential playback by the user and placed in logical storage unit 153, and the logical contents of the virtual storage unit 153 may be modified (by the addition or deletion of advertising, for example) and placed in the virtual storage unit 163. When program data is logically transferred form storage unit 143 to 147, and then from unit 147 to unit 153, it becomes increasingly insulated from destruction. In general, content, which has not been selected by the parsing process at 145, is eligible to be overwritten, as are parsed program segments, which are "discarded" at step 151. In fact, unparsed and discarded content is not actually overwritten until additional space is required to store new incoming broadcast content.

Note also that, as long as program content contiguous to any program segment stored in virtual storage units 147, 153 and 163 has not been overwritten, the start and end boundaries of these virtually stored segments may be modified since the location and extent of each such program segment is defined by metadata and not by separate storage. In a similar fashion, the storage unit 107 at the server is preferably a virtual store whose logical contents are defined by metadata, which specifies programming content stored in the input store 103. As described later in connection with playlists, if a user is viewing or listening to a given program segment, he or she may issue command to "continue playing" a given segment beyond its end boundary, enabling the context of a segment to be reviewed. In the same way, content which continues to be available in the "inbox" storage 143 before the start boundary indicated for the program segment may be reviewed as well on request.

The system may capture more than one copy of a given program segment (e.g. song) if desired. Multiple copies may be compared in order to create a better single copy. For example, two or more copies can be "averaged" to accentuate shared components and suppress noise or talkover components existing on only one recording. After duplicates are processed, the extra copies may be discarded to save storage space. In addition, editing facilities at 135 permit the editor to readily compare the two copies of a given program segment select the better of the two for inclusion in the program library. The user may also rate the quality of a particular program segment, or the quality of programming available from a particular source, to facilitate the elimination of less desirable duplicates.

When Community Markup (CM) is used to enable users to share metadata and program quality ratings, an automatic search may be performed for best of several copies. With a community markup scheme, metadata, including song quality, is stored at the central server at 113, or shared among users on a peer-to-peer basis. For example, such community-generated metadata may accordingly be used to determine if the quality of a new copy is better than a previously recorded copy in a personal library. Thus, a previously recorded copy having a reduced rating due to DJ talkover could be automatically replaced by a recently received higher rated copy.

"A user might collect hundreds of program segments with just a few days of recording of broadcast materials. Cleaning out the "inbox storage" at 143 and selectively deleting unwanted songs, even if there are duplicates would require a prohibitive effort by the user. Therefore, any method of helping the user make a decision quickly about the desirability of a song would help this process. To this end, the server could make available thumbnail summaries or short snippets of each program segment identified in the database, or the metadata could include a designation of a snippet, and these snippets could then be presented to the user to facilitate the save/delete selection process."

The availability of snippet identification data also enables the user to more quickly scan the program segments or songs available in the library. These snippets may be presented in succession to the user, in a fashion similar to the manner in which a car radio scans sequentially scans from station to station until interrupted. Because each snippet identifies the readily recognizable "sweet spot" of each program segment, the program segments may be readily identified by the user. The user may also manually scan from snippet to snippet by pressing a "Next" button when hands-free scanning is not desired. Either way, the user can use the recorded snippets to more readily select desired program segments during playback, or to skim through the recently deposited program segments which have been initially parsed at 145 to make quick manual select/discard decisions at 151 regarding the desirability of keeping a given program segment.

Business Models

The creation and distribution of metadata relating to broadcast programming may be sponsored by a variety of business models.

The metadata may be distributed on a subscription basis, with each user paying a fee to the metadata provider. The use of metadata may be accompanied by the presentation of advertising presented along with the programming content either by modifying the content as illustrated at 161 in FIG. 1. Advertising revenue may also be derived from the presentation of promotional material when program guide information is displayed, or when editing screens are displayed that enable users to generate comments or program recommendations. "Public" authors of metadata, which is shared with others, could be compensated on a commission basis, or could receive discounts from subscription fees in return for supplying metadata to others. For example, metadata created by a markup editor could be compensated with a pro-rated share of revenues based on how many of his or her metadata items were used compared to the total system-wide use of metadata.

Individual users may be compensated for watching advertising, and this compensation may take the form of a reduction in subscription fees or an actual payment. Note that, by using user preference data to direct advertising to those who would have the greatest interest in the specific service or product advertised, both the advertiser and the user are better served. Advertisers reach those potential customers having the greatest potential interest in the advertised material, and users need not be burdened with the presentation of advertising in which they have no interest.

When advertising that is provided as part of the content programming, or inserted into the content as noted above, the user may press an "information" button (normally used to trigger a display describing the program currently being played) to obtain additional information about the advertised product. In this way, the user identifies products and services about which he or she has a particular interest, and the advertiser is able to provide information (including the URL of an Internet resource containing detailed information), which would otherwise be unavailable to the user.

A remote control device may be used to accept positive or negative rating metadata during a program without interrupting the program. For example, the viewer may press a positive rating button on the remote control device one or more times to signal a level of recommendation, or press a negative rating button one or more times to signal a level of disapproval.

When previously parsed programming segments are being played to the user, the user can issue a request to insert a comment or annotation at any time during a segment. Then, at the end of the segments, a display screen or other prompt will appear. In this way, the playback unit can accept a comment, annotation, rating, or the like at the end of the segment. If live broadcasting is being viewed, the incoming broadcast can be recorded so that viewing can then be resumed on a time-shifted basis after the metadata is created.

During playback of segments having associated metadata, the viewer may select the manner in which the metadata is presented. For example, descriptive comments may be displayed as close-captioned text or in a separate screen window without interrupting the program display, or the metadata may be displayed at the beginning to aid the view in determining whether or not to watch the program or program segment about to be displayed.

The technique of broadcasting programs (content) for storage at the user's location and thereafter performing time-shifted playback under metadata control may be used as a primary system of program distribution by content owners (record companies, broadcasting networks and stations, etc.).

For example, radio or television programming could be broadcast in compressed and/or encrypted form for local storage, a "record selection" file of metadata may then be used to selective record programming of probable interest to the user at the user location, and the resulting programming may then be selected for inclusion in the user's program library and selected for playback under user control as described herein. The cost of programming could be financially supported in whole or in part by subscription fees, or by advertising, and users could elect the extent to which they were willing to view advertising in exchange for reduced subscription fees. Advertising segments, like programming content, may be inserted into the programming at playback time and selected based on user preferences and demographics, helping to insure that the advertising presented is relevant to the consumer and hence of more value to the advertiser and the consumer. With the consent of the copyright owners, radio and television broadcasts would enable users to purchase music singles, entire CDs, music videos and complete movies for inclusion in their personal radio and/or television program library. Program catalogs distributed in advance of the broadcast could be used to alert the user to future broadcast programming that could be recorded under metadata control at the time of broadcast distribution.

With or without pre-published catalogs and playlists, content owners and broadcasters could use a content watermarking system, or identification codes imbedded in the program as broadcast (for example, using the RDS standard) to make it possible to identify program segments regardless of the time and frequency of the broadcast. In this way, watermarking and identification code systems used for other purposes (e.g. broadcast monitoring for royalty verification, or to prevent illegal copying) could be used for the additional purpose of controlling recording and playback by licensed users under metadata control. Identification codes or watermark patterns may be included combined in huntlist and playlist metadata data with additional metadata describing the identified programs.

To promote particular songs, albums, subscription or free broadcast programming, record companies and broadcasters might distribute metadata, which presented selected segments of recorded programming in organized "previews" designed to promote individual program segments. Sample songs and programs might be made available free of charge to promote related programming, in which case mechanisms could be included minimize any possible cannibalization of program sales, but while providing introductory exposure to new programming. As such, the following features might be implemented:

1. Restricting how many songs off an individual album, or how many programs from serialized programming, could be captured.
2. Limit the duration of any preview segment.
3. Limiting the size of the "preview" library.
4. Limit the "life" (duration) that a program may be previewed, or limit the number of times a program segment (e.g. audio song or music video) can be played before it must be purchased or paid for on a use basis.
5. Charging a subscription fee for the right to view preview copies
6. Prevent preview segments from being transferred to another user.
7. Inserting advertising into previews.

Selecting and Modifying Content at the User Location

As indicated at 143-171 in FIG. 1, the metadata provided by the remote facility, or by other users, or by the local user, may control the selective recording and rearrangement of program segments to form composite programming. Thus, segments extracted from several news programs might be recorded during the day with all programming dealing with a particular topic being consolidated into a single composite program devoted to that topic. The selection of the components of such a composite program may be made at the remote location by using the preference data supplied by an individual user stored at 117, or may be done at the user location by matching locally stored preference data against program description metadata received from the other locations or locally produced descriptive metadata. Note also that such a composite program need not be constructed in advance at 161 and stored at 163 for playback, but may instead be assembled "on-the-fly" simply by selecting identified segments in the proper order from the segment store 147.

Selecting Segments for Playback at the User Location

As noted earlier, the metadata, which is available to the user, may include electronic program guide (EPG) data for displaying a listing or matrix of available programming, including both live programming and recorded programming. The user may select items from this EPG display to record or play incoming broadcasts (or both), may play previously recorded programming, or may identify future programming to be recorded.

During playback of recorded material, and during the recording of new material, a progress bar that shows the location within a program that is currently being viewed can be displayed at the user's requests, typically occupying only a portion of the screen while the video content occupies the remainder. Segment markers can be noted on the bar and associated with icons to indicate the presence of descriptive metadata. Using a mouse or remote control to "click on" or select a segment displayed on the content bar would then alternatively cause the metadata associated with that segment to be displayed, or would resume playback of content at the beginning of the selected segment. Segments as shown on the progress bar could be color coded based on a program rating to enable the user to quickly view highly rated segments, or to skip lower rated segments.

In addition, metadata about segment quality or other attributes may be displayed on the screen using suggestive icons (smiling faces, frowning faces, etc.) while a segment is being shown helping viewers to more quickly decide whether to hit the "next segment" button or a channel surfing button on a remote control unit. Icons indicating the availability of additional descriptive metadata may also be displayed on the progress bar, or associated with programs listed in a displayed program guide.

Because metadata may exist in many forms from many sources, the user may be given the opportunity to enter display preferences that control the manner in which metadata is displayed. Thus, metadata from especially trusted sources may be preempt regular programming and be provided with use of the entire screens, while other metadata may be displayed as closed captioned text or as icons, or without any display unless the view specifically requests the presentation of metadata for a particular program segment.

One of the most important mechanisms for assisting a user in locating desirable programming is the use of metadata to enhance the content and operation of the electronic program guide. Metadata indicating a user's preferences which is derived from both the preferences directly expressed by the viewer and by preferences inferred from the user's viewing and metadata creation activities may be used to selectively display and highlight particular programs in the program guide listing. Icons or highlighting may be used to identify listed programs and segments for which additional metadata is available for display to the user upon request. Metadata which ranks programs may be displayed using rating icons, color coding, or highlighting to guide the viewer toward higher rated programs.

Note that program guides may display listing of previously broadcast materials which are available in local storage, broadcast programming which will be available currently and in the future for viewing and recording, and "content on demand" programming which exists as retrievable resources on program servers and on storage maintained by other users and shared on a peer-to-peer basis with other users. Metadata describing all such programming content may be located using an electronic program guide format which permits the extensible display of additional metadata and the selection of particular program content for viewing and recording.

Playlists

The metadata, which describes individual program segments, may be combined to form an ordered playlist. As described in detail in U.S. Pat. Nos. 5,271,811, 5,732,216, and 6,199,076, and in co-pending application Ser. No. 09/782,546 filed on Feb. 13, 2001, by James D. Logan et al., by James D. Logan et al., the metadata as assembled at the server and transmitted to the user location may take the form of a playlist consisting of a scheduling file of metadata which specifies the content and schedules a default playback sequence in which that content is reproduced. At the user station, the scheduling file may be reorganized to alter the content and schedule of a playback session. As described in the foregoing patents and application, the content of the playlist may be varied in accordance with preferences associated with each user.

The metadata stored at 133 is available to the user to facilitate the selection and navigation of available program materials. The metadata may include a playlist that specifies the sequence within which program segments will be played back. Navigation controls including skip forward and skip backward controls may be used to skip the remainder of the segment being played and resume the playback at the beginning of the next segment, at the beginning of the current segment, or the beginning of the prior segment.

In addition, the user can vary the playback speed, request compressed playback where periods of silence and/or unchanging images are skipped. Playback speed can be automatically increased (both speech and video) under metadata control or by analysis of the content when the action is minimal (e.g. huddles in a football game) and slow down when the action picks up (e.g., after the football is put in play). Sequences that are candidates for rapid replay may be specified by metadata or can be determined by identifying programming when no voices are present in the audio component and minimal changes are occurring in the video image. Automatic or manual playback speed adjustments may applied independently to different program streams displayed concurrently in a split screen or in a picture-in-picture (PIP) display. As noted elsewhere, a viewer's decision to skip, speed up or slow the display of a particular segment may be used in a segment rating system as vote indicating that viewer's level of interest in that segment. In addition, such viewer actions can be used as an indication of the viewer's subject preference or disinterest in the subject matter of that segment and such decisions, on a cumulative basis, can be used to develop a preference profile used to automatically recommend or select programming for recording or playback.

Metadata may also be employed to specify a play list composed of extracts from a stored program, enabling users to view a preprogrammed preview of a given program, or to view a shortened summary of the program instead of the entirety of the program. When passages of particular interest to the viewer are presented, the user may be given the option of viewing that segment in its full context, and then switch back to the shortened version on demand. Note that a decision by a viewer to switch to the full context for a particular segment presented in a preview or summary may be taken into account as a positive rating for that segment, or as a preference indication attributable to that viewer. As noted elsewhere, the "snippets" which are viewed or listened to during playlist navigation or scanning may a highlight or "sweet spot" of the program segment which is designated by metadata.

Metadata labels may be displayed in a list, or as subtitles, to assist the user in rapidly locating desired segments for playback. A mosaic of images, each selected from a single segment, may be displayed as a visual cue to assist the viewer in locating a desired segment from a sequence of segments. When the metadata includes descriptive text, keyword searches can be performed to identify segments described with matching words.

The presentation of probable preferences, whether by icon display, highlighting particular items on a program guide listing, or the like, may be based on either a local or remote analysis comparison of the user's preference profile with the metadata that describes the segment's program content. If done remotely, icons and highlight control metadata may be sent with the program guide or programming material to directly control the user's display whereas, if the analysis is performed locally by comparing locally stored preference data with the descriptive metadata, the user's privacy may be better protected since preference information need not be transmitted outside the user's location.

The subdivision of program materials into logical segments makes it possible for a viewer to save individual program segments, and their associated descriptive metadata, into a virtual scrapbook consisting of segments tagged as saved for later viewing. If desired, a viewer may edit such a scrapbook play list to delete or crop particular segments, rearrange the sequence in which they are to be played back, and add annotations or comments. The resulting program sequence can then be persistently stored in the available local storage area, or transmitted as message containing both content and metadata to another user. The user may also be provided with the ability to record the fact that a particular program segments was found to be particularly interesting or enjoyable, thereby affirmatively recording a preference for further installments of the program and/or for other future or recorded programs having similar content. Note that the act of saving a given program or program segment into the user's scrapbook may be recorded as positive vote in that program or segment's approval ranking, and as an indication of the subject matter interests of the viewer.

Also, while viewing a particular program segment, the user may be given the option of deleting that segment from storage, deleting an entire program sequence to which that program belongs, or affirmatively recording dislike for programs of that type which can be taken into account when the preference makeup for that user is employed to automatically select, recommend, or discard different programs and program segments.

In order to create truly personalized radio or television, it is desirable to create playlists on a continuing basis. In addition, it is desirable to allow users to create their own playlists and to randomize these playlists to automate the sequence in which selected program segments are played, or to automatically play those segments in a random sequence.

The central server, or the local system, may generate playlists based on a combination of shared and personal data. The shared data may identify program segments (e.g.

songs or informational segments), which go together and further indicate a preferred playback sequence for associated segments. The personal data may be based on the user data (locally available or uploaded to the server and stored at 117), which may identify which program segments are available to the user and which segments have been previously played, and when. This shared and personal data is then processed to produce a recommended personalized playlist, which is made available to automate the user's playback sessions.

In order to have the server-based playlist generation mechanism work well, it needs to know as much as possible about the user's demographics, expressed preferences, listening habits and experiences. As described in U.S. Pat. Nos. 5,271,811, 5,732,216, and 6,199,076, the content of the scheduling metadata (playlist) may determined from the weighted combination of the user's demographic characteristics, expressed subject matter preferences (e.g. particular music genres and artists), and "log file" data which identifies what, when and how the user previously played. At the time of playback, the user may also specify a positive or negative rating to the segment being played. (See also, the discussion of the negative rating "Never again" button and the positive rating "huntlist") discussed separately.

In addition, to tracking recorded program segments actually played, the log file may advantageously record the identity of live broadcast programming or programming from physical media or other sources (e.g. music or movies on compact disk, downloaded MP3 files, etc.) which is viewed or listened to.

The user may designate a preferred session length for the playlist. Thus, in a radio based system for use by commuters, the session length may be related to the average transit time to or from work. Only those program segments having the highest positive weighted rating and which, together with other high rated program, have an combined playing time that approximates the requested session length are included in the playlist.

Playlists, program guide data, and compilations from other sources may be aggregated and presented to the user. For example, the server or the user location may employ a searchable database of available program materials (e.g. songs, albums, movies, etc.), which the user may use to select a list of desired programming. This desired program list may then be used to form a huntlist for broadcast programming saved to the inbox storage at 143, to transmit to the server as user preference information, or to provide an indication of the user's subject matter preferences which can be used identify related available programming which the user may wish to view or listen to.

Additional implicit metadata regarding user preferences by may be derived by monitoring other forms of users' interaction with music. When the user change broadcast stations when viewing live broadcasting, skips a song being played from a playlist, or rejects particular program segments from a server produced catalog of available programming, a negative rating for that program segment can be inferred. Conversely, when the user plays a song or program segment multiple times, requests additional information about a program segment or artist, etc., this behavior can be interpreted as a positive indication for that program or subject. Song preference metadata of all types will be used with our Selector-type program to optimize the construction of a personal radio station. Alternatively, the data may be ported over and used by a subscription music service.

The user interface presented to a user for program library and playlist management may be designed using the interface for an email client as a metaphor. Just as email is "pushed" at the user and then sorted, read, and filed, a playlist manager presents a list of program segments that are available in the user's personal library. Programs, which have previously been played, may be identified by a distinctive type font or color. Once listened to, the style in which the program segment is listed is changed. Users may sort the program listing list by artist, program name, date and time of capture, source (e.g. radio station call letters), recording quality, user rating, and other parameters. Multiple sort fields will be allowed; for example, the listing could be sorted by source first, and then by time of capture. Any program on the list may be selected (by clicking or by entering its list number). When selected, a given program listing may be immediately played in its entirety, a "sweet spot snippet" only may be played as a preview, or the selected segment may be added to a playlist, or moved to a user-created and user-named "folder," or to a system-created folder.

Metadata which indicates the subject matter category or categories (or genre) to which a program segment belongs, or indicates the artist name, album name, or series name may be used to create an initial set of system-created folders and sub-folders for program segments. Users may move individual program segments to and from these folders and user created folders. When a request to delete a program segment in one folder is issued, and the same program segment also exists in other folders, the user may be given the option of deleting that program segments from all folders at once. A "trash" folder may hold a listing of all deleted program segments which are, in fact, retained in storage until the contents of the "trash" folder are deleted in whole or in part (in the same manner that a "trash folder" in many email clients operates). Category indicating icons, different font colors and styles, etc. may be used on any single listing to assist the user in visually selecting particular program segments.

Program segments identified in a playlist or folder may be shared with others; that is, the metadata may be transmitted to others for inclusion in their huntlists or program library if the underlying material is already available, along with a covering "forwarding memo" from the sender. Metadata may be transferred in a standard format as a MIME attachment to email, or may be shared using other forms of peer-to-peer transfer.

An application particularly suitable to video, the user might prefer an alternative to working off of a list, which could require the user to go back and forth between the list and the video screen. In this case, program listings and selection menus may be superimposed over the image, or in window or frame adjacent to the viewing area. Visual prompts, which characterize the currently viewed programming, may also be displayed. For instance, short descriptions of the program segment, a rating value, an indication of the source and time of the original broadcast, or any other information derived from the metadata may be displayed concurrently with the program.

Navigation cues can be displayed, such as a "forward arrow" shown on the screen during a low rated segment, encouraging the user to skip to the next program on the playlist. For video or audio, the user might want to have more data available at once and so multiple icons may be shown on the screen at once. By skipping to last of four forward arrows, the user might jump ahead four segments. By the form or color of the icons may indicate each corresponding segment's rating or subject matter, permitting the user to more easily directly to a desired segment. A linear map of the content of the playlist, or of the currently playing program segment, might be presented across the bottom of the screen, letting the user go right to a desired segment or scene. The user may also be given the ability to modify the playlist by highlighting programming to be skipped. In addition to skipping or deleting segments (negative actions) another user interaction could be to "seek" or find similar segments immediately, or a request to include such similar segments on the user's huntlist. In addition, the user may elect n to "continue" playing a given segment beyond the end boundary indicated by the metadata for that segment, or to review program material broadcast before the start boundary for that segment.

With a handheld device, the user could hold the skip button down for an extended time and that action would delete or skip over all segments similar or associated with that segment. Attributes could be on the screen that the user could click that would preface the second action of deleting or finding etc. In addition to deleting non-qualifying segments, the system could rearrange segments. Again, this could be done with varying levels of user involvement, reaffirming the feature each time or setting a preference for rearrangement once. In a more automatic system, the user could re-select preferences each session. The segments would be compared against these preferences and non-qualifying segments cancelled. More automatic, would just be a reaffirmation of existing preferences.

Playlist control is not limited to specifying recorded segments. For example, a commuter may wish to listen to a program of recorded music from a playlist, but further specify that the recorded playback is to be interrupted at predetermined times to permit the user to listen to a favorite scheduled news, weather or traffic report as a live broadcast. In this case, the playlist includes the designation of both live and recorded programming and dynamically alters the playlist so that live programming can be played at its broadcast time. Because the playlist can control the tuner or tuners, the user can be presented with a hands-free combination of selected live and pre-recorded programming. To assemble such a playlist, the metadata provided from the server includes program guide data for future programming. To the extent such programming is serialized, the user may request that a given live program segment be dynamically included in any playlist, thus effectively "interrupting" scheduled recorded programming to bring the user each pre-selected live broadcast.

Advertising Preservation

It may be important to prevent the user from skipping the advertising, which provides financial support to the broadcaster and others. To this end, segment start and end marks may be placed in such a way that the advertising, which supports a segment, is always included in the segment. The advertising could also be placed in a "skip protection" zone. For example, if a program segment was supported by advertising content at both the beginning and end of the segment, an attempt to skip the advertising played at the beginning of the segment would cause the player to skip to the beginning of the next segment (thus preventing the user from playing the content without first listening to the leading advertising segment. Any attempt to skip the advertising at the end of the segment would simply be ignored.

In the community markup system, editors contributing markup would be prohibited from placing skip marks in a fashion that would permit advertising to be skipped without also skipping the supported content.

Selecting Program Sources

A user typically has many different broadcast stations to choose from, and recording all broadcasts from all stations would exhaust, or at least misuse, local system resources. Accordingly, it is desirable to provide mechanisms for automating or assisting the user in the selection of program sources to record. Typically, this selection is made based on both frequency and time; that is, selecting different frequency channels at different times to capture programming of the greatest interest to the user.

Because the server typically has a database which indicates what program segments were broadcast by what stations over a time interval of recent days or weeks, and because the server further has available to it information from the user containing user preference information, including requests for particular programs, for particular series of programs, for particular subject matter categories or genres, for particular artists, and the like, it is possible to match the user preferences against the broadcast histories of those sources which are accessible to the user and provide the user with data indicating which stations are most likely to broadcast subject matter of interest to the user, and a what times. Since the user typically has only one or a few tuners available, and/or a limited capability to record plural programs at the same time, and limited storage space, predictive tuning may be applied to increase the likelihood that programming will be captured which best fits the user's preferences.

Thus, the user's huntlist of desired programs, together with preference information which is expressly provided by the user or implied for the user's prior selection history, is used to develop a recording schedule file which identifies particular stations and the times of day when those stations typically broadcast programming of interest to that viewer. This recording scheduling file of metadata is then downloaded from the server to the client location and used to control the selection of program material received and stored in the inbox storage 143. Alternatively, the recording schedule file may be used to recommend a recording schedule to the user, thus alerting the user to desirable recording opportunities that might otherwise be overlooked. For example, the recording schedule file may be used to highlight sections of an electronic program guide to assist the user in making informed selections of particular programs of interest. When a recording selection file is used to automate the recording process (typically without requiring the attention of the user), the content of that file may be transmitted to the server so that the server can then return a program segment identification file which identifies the content of programming recorded, and permits individual recorded segments to be selected by the user, or automatically compared with the user's huntlist to select desired programming for inclusion in the user's library.

The "record selection file" may also be used to provide "hands free" automated tuning of live radio broadcasts. The record selection file developed based on the broadcast history of available stations and on the user's preferences may be used to supplement a listing identifying those programs which are specifically requested, with the result that the system makes an informed "guess" about the station most likely to broadcast live programming of interest. Normally, however, it will be preferable to allow the system to record programming in advance to create a library of program segments which are of know interest to the user, and then to insert these programs on a time shifted basis between specific live broadcasts identified by the user.

Live and time shifted broadcast programming may be organized by genre, permitting the user to select a specific type of programming. For example, the station selection push buttons in a car radio might be associated with different kinds of programming: a "news" button would play the most recent news broadcast from the beginning on a time shifted basis; a "traffic" button would play the most recent traffic report; and "classical," "jazz" and "alternative" buttons would play back recently recorded music in each specified genre. The user would pre-assign the kind of programming desired, and a "record selection" list calculated to capture desired programming in each category would be provided to the user. Programming which is time sensitive (traffic reports having a high priority, news programming a medium priority, and music having a low priority) would take precedence to insure that recently broadcast information is always available.

CONCLUSION

It is to be understood that the specific methods and apparatus that have been described are merely illustrative applications of the principles of the present invention. Numerous modifications may be made to the processes and mechanisms described without departing from the true spirit and scope of the invention.

What is claimed is:

1. A method of processing digital video using at least one computer, the method comprising:
   receiving, at the at least one computer of a first user, a first digital video;
   subdividing, at the at least one computer, the first digital video into a plurality of segments;
   generating, at the at least one computer, metadata regarding the first digital video, the metadata identifying at least one splice point that demarks at least one segment of the plurality of segments of the first digital video;
   electronically transmitting the metadata from the at least one computer to a plurality of computers of a plurality of users other than the first user via a wide area network for redistribution by the plurality of computers;
   receiving, at the at least one computer of the first user, the metadata redistributed from a second computer of a second user of the plurality of computers;
   wherein the metadata includes instructions adapted for use by the destination in automatically substituting a second digital video for the segment at a splice point of the at least one splice point of the first digital video or automatically skipping the segment beginning at the splice point;
   wherein the metadata is editable by any of the plurality of users and redistributable among the plurality of users including the first user.

2. The method of claim 1, wherein:
   the splice point is a first splice point;
   receiving also includes receiving first digital audio at the at least one computer that received the first digital video, the first digital audio corresponding to the first digital video;
   generating includes generating the metadata in a manner to also identify a second splice point that demarks a segment of the first digital audio;
   the metadata is to include instructions adapted for use by the plurality of computers of the plurality of users other than the first user in automatically substituting second digital audio which corresponds to said second digital video at the second splice point; and
   electronically transmitting the first digital audio to the plurality of computers of the plurality of users other than the first user.

3. The method of claim 2, wherein electronically transmitting comprises transmitting the first digital video as compressed video to the plurality of computers of the plurality of users other than the first user and transmitting the first digital audio as compressed audio to the plurality of computers of the plurality of users other than the first user, and wherein the first splice point and the second splice point correspond to different times relative to the compressed video.

4. The method of claim 1, wherein:
   the instructions include instructions to retrieve the second digital video from a source other than the at least one computer, from over the wide area network.

5. The method of claim 1, wherein:
   the splice point is a splice-in point;
   generating includes generating the metadata to also identify a splice-out point; and the splice-in point and the splice-out point are to demark the segment.

6. The method of claim 1, wherein:
   the second digital video comprises advertising.

* * * * *

UNITED STATES PATENT AND TRADEMARK OFFICE
CERTIFICATE OF CORRECTION

PATENT NO.          : 10,313,714 B2
APPLICATION NO.     : 14/284367
DATED               : June 4, 2019
INVENTOR(S)         : Logan Page 1 of 1

It is certified that error appears in the above-identified patent and that said Letters Patent is hereby corrected as shown below:

In the Claims

At Column 41, Claim 1, Line 46, please remove "destination" and insert --plurality of computers of the plurality of users other than the first user--.

Signed and Sealed this
Sixth Day of August, 2019

Andrei Iancu
*Director of the United States Patent and Trademark Office*